United States Patent [19]
Wade et al.

[11] Patent Number: 5,695,720
[45] Date of Patent: Dec. 9, 1997

[54] FLOW ANALYSIS NETWORK APPARATUS

[75] Inventors: Adrian P. Wade, Richmond; James McKinley, North Vancouver, both of Canada

[73] Assignee: B.C. Research Inc., Vancouver, Canada

[21] Appl. No.: 416,604

[22] Filed: Apr. 4, 1995

[51] Int. Cl.$^6$ .................................................. G01N 21/08
[52] U.S. Cl. ........................... 422/82; 422/67; 422/68.1; 422/81; 422/62; 436/52; 73/863.41; 73/864.81; 356/36; 356/442
[58] Field of Search .......................... 422/62, 67, 68.1, 422/81, 82, 82.05; 436/52; 73/863.41, 864.81; 356/36, 442

[56] References Cited

U.S. PATENT DOCUMENTS

| | | | |
|---|---|---|---|
| 3,871,826 | 3/1975 | Bakay | 23/230 R |
| 4,022,575 | 5/1977 | Hansen et al. | 73/425.4 R X |
| 4,224,033 | 9/1980 | Hansen et al. | |
| 4,227,973 | 10/1980 | Ruzicka et al. | |
| 4,314,824 | 2/1982 | Hansen et al. | |
| 4,486,097 | 12/1984 | Riley | 356/410 |
| 4,517,302 | 5/1985 | Saros | 436/180 |
| 4,610,544 | 9/1986 | Riley | 356/410 |
| 4,680,270 | 7/1987 | Mitsumaki et al. | |
| 4,726,929 | 2/1988 | Gropper et al. | 422/68 |
| 4,819,478 | 4/1989 | Melcher | |
| 4,865,811 | 9/1989 | Newton et al. | 422/81 |
| 4,920,056 | 4/1990 | Dasgupta | 436/50 |
| 4,958,295 | 9/1990 | Davidson et al. | |
| 4,974,592 | 12/1990 | Branco | |
| 5,080,866 | 1/1992 | Petty et al. | 422/80 |
| 5,087,425 | 2/1992 | Flossdorf et al. | |
| 5,182,617 | 1/1993 | Yoneyama et al. | 356/440 |
| 5,196,169 | 3/1993 | Schick et al. | 422/81 |
| 5,240,681 | 8/1993 | O'Lear et al. | 422/82 |

FOREIGN PATENT DOCUMENTS

| | | | |
|---|---|---|---|
| 60-107541 A | 6/1985 | Japan | G01N 1/00 |

OTHER PUBLICATIONS

Ari Lvaska et al., "From Flow Injection to Sequential Injection: Comparison of Methodologies and Selection of Liquid Drives", Analyst, Jul., 1993, vol. 118, pp. 885–889, Feb. 11, 1992.

Adrian P. Wade, Paprican Report to Industry, #4, pp. 16–17, Jan., 1993.

Adrian P. Wade, Paprican Report to Industry, #5, p. 16, Apr., 1993.

Adrian P. Wade, Paprican Report to Industry, #6, pp. 14–15, Jan., 1994.

Univ. of British Columbia Pulp & Paper Centre Annual Report, Jul. 1, 1992–Jun. 30, 1993, Dept. of Chemistry, pp. 380–40.

Univ. of British Columbia Pulp & Paper Centre Annual Report, Jul. 1, 1993–Jun. 30, 1994, Dept. of Chemistry, pp. 34–35.

Miguel Gugman & Bruce J. Compton, Talanta 1993, 40, #12, pp. 1943–1950.

(List continued on next page.)

*Primary Examiner*—Harold Pyon
*Attorney, Agent, or Firm*—Bell, Boyd & Lloyd

[57] ABSTRACT

A computer-controlled fluid manipulation and analysis apparatus for chemical, biochemical and clinical analysis, sample preparation, and microscale chemical and biochemical synthesis, having one or more stream selection hubs with multiple ports through which microliter volumes of multiple fluid streams may be accessed, stacked, mixed and otherwise transferred by two or more cooperant pumping systems in a highly repeatable and fully software programmable manner. The inherent or resulting properties of said fluids may be automatically recorded via one or more appropriate electronic detectors and data recording systems. Systems comprised of two or more hubs exhibit higher properties of a flow network, and allow more than one fluid segment to be processed simultaneously. Bi-directional flow may occur in each inter-hub connection, and a plurality of possible transport routes can exist between hubs. This leads to enhanced flexibility in sequential processing of each fluid segment.

23 Claims, 18 Drawing Sheets

OTHER PUBLICATIONS

Adrian P. Wade, Univ. of British Columbia, Pulp & Paper Centre, Annual Report, Jul. 1, 1991–Jun. 30, 1992, pp. 32–37.

Mechanical & Chemimechanical Wood Pulp Network Annual Report, 1992–93, p. 88.

Adrian P. Wade and M.D. Kester, See Abstract from FACSS Conference, Oct. 17–22, 1933, Manhattan, Kansas.

Adrian P. Wade & Michael D. Kester, Abstract from Flow Injection Analysis, Winter FIA Conf., Jan. 1994, San Diego, CA (see loose leaf sheet "X") and FACSS Conference, Oct. 1994.

M. Gugman et al. Talanta, 40, #1, pp. 81–87, 1993.

Rugicka et al. Analyst, Jul., 1993, 118, pp. 885–889.

Rugicka et al. "Analytical Chemistry", 1990, 62, pp. 1861–1866.

G. W. Kramer "Robotics in the Industrial Laboratory"—PASS—ACS Symposium Series Monograph.

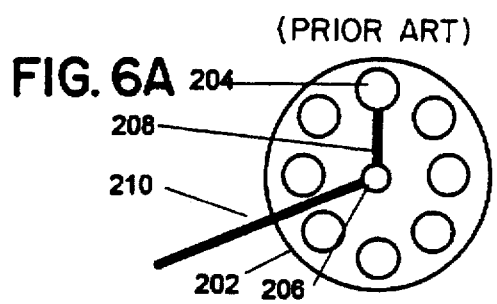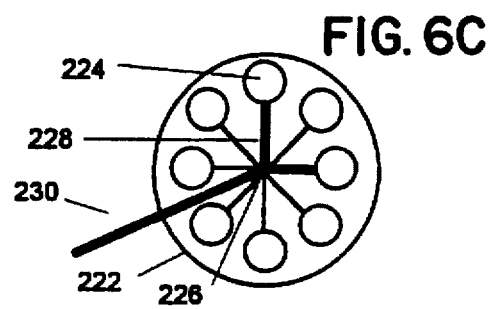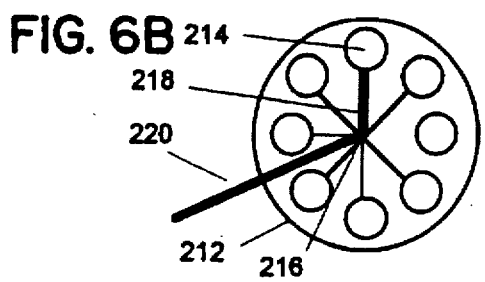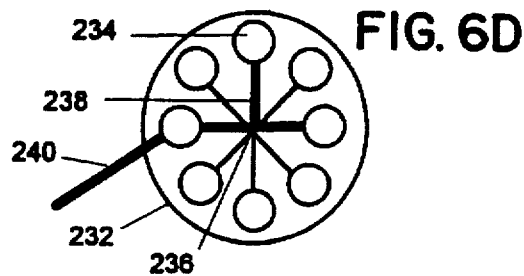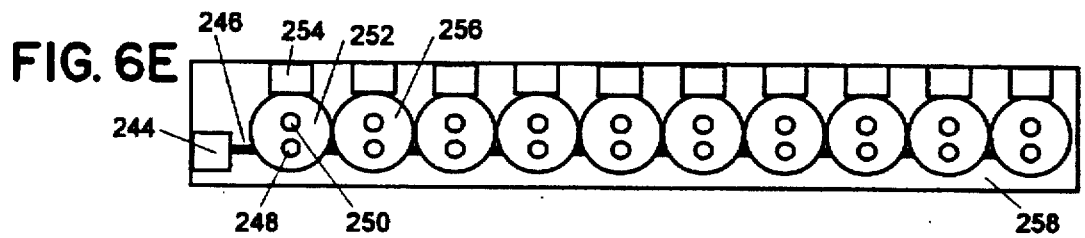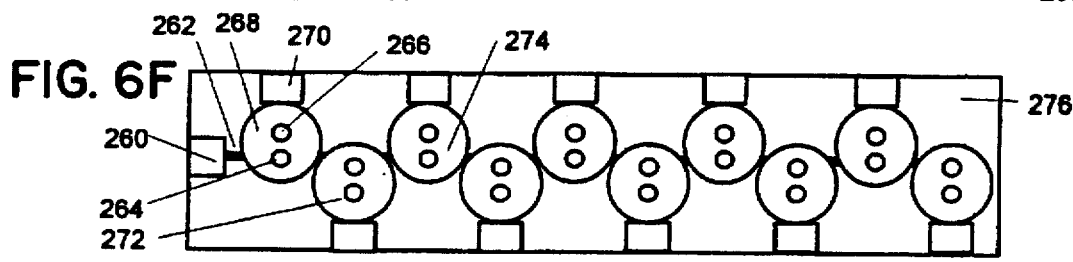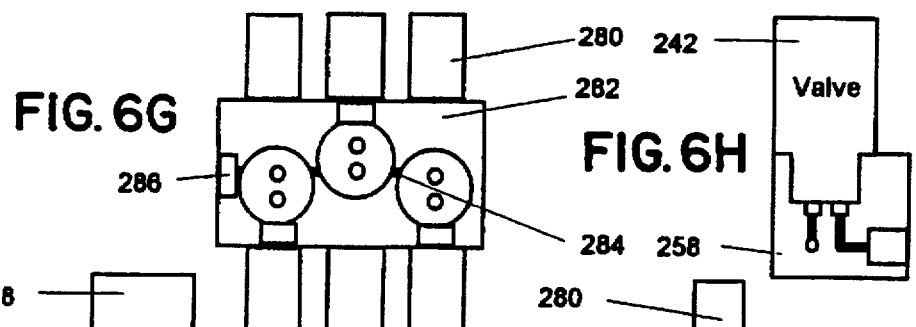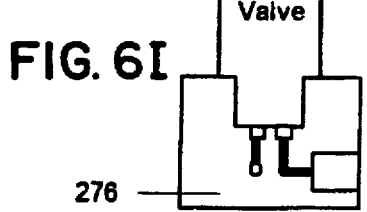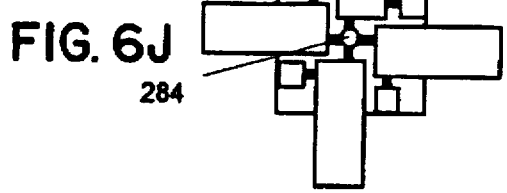

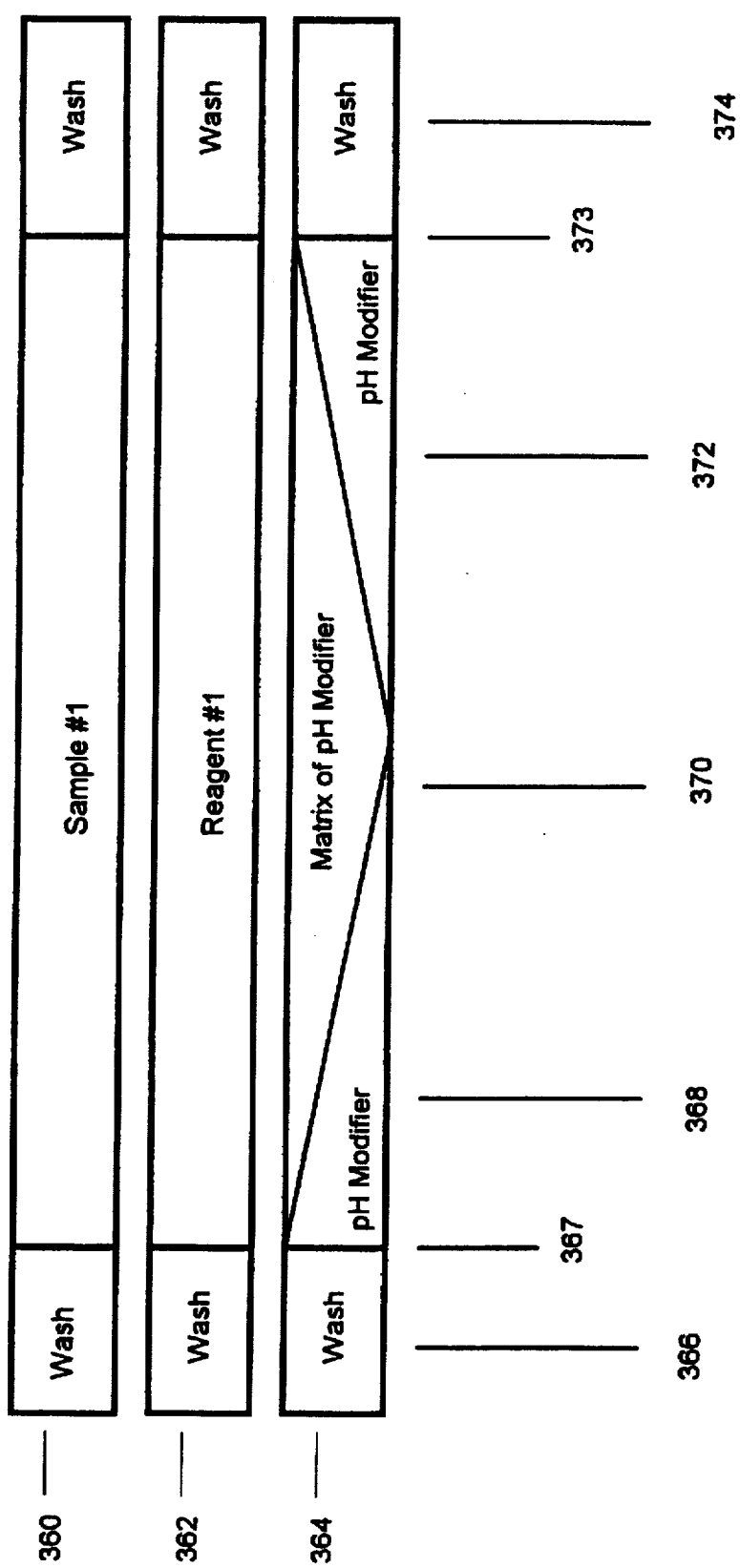

FLOW ANALYSIS NETWORK APPARATUS

FIELD OF THE INVENTION

This invention relates to apparatus and methods of liquid and gaseous fluid manipulation for the analysis of chemical, biochemical and clinical systems, sample preparation, micro,-scale chemical and biochemical synthesis and, particularly, computer controlled apparatus for said purposes.

BACKGROUND OF THE INVENTION

Air-segmented Continuous Flow Analysis is known which involves a collection of interconnecting conduits of fixed geometry through which solutions containing reagent and sample are propelled, typically, by means of a peristaltic pump. The liquid streams are segmented by air bubbles such that an individual sample is distributed among 15-20 liquid segments. Segments containing successive sample volumes are separated by liquid segments containing wash solution. Sample solutions are introduced by aspiration, rather than by injection valve. Reaction between analytes present in sample solutions and reagents can occur within each fluid segment, indeed, the presence of the bubbles provides a tumbling mechanism which causes effective mixing. Segmented continuous flow systems using segmenting fluids other than air are known.

Flow Injection Analysis (FIA) involves injection of a discrete volume of sample solution into a carrier stream usually carried out by an injection valve, such as a low pressure, chemically inert equivalent of the type used in high performance liquid chromatography (HPLC). The stream into which the sample has been injected may contain chemically selective reagents and may be merged with other streams en route to a detector. Reactions may occur within the streams to produce a detectable product, or the detector may sense some intrinsic property of the sample itself.

Sequential Injection Analysis (SIA) involves the use of an apparatus comprising, typically, a rotary valve around which multiple liquid solutions are arranged, a pump and coil arrangement whereby segments of selected solutions can be accessed via the valve and stacked in sequence in the coil and a detector attached to one port of the valve via which the stacked segments can be made to flow by the pump. Stacking is the process of providing a plurality of aliquots, slugs or segments of fluids in a single conduit, either discreet and apart one slug or aliquot from another or adjacent to one another. The segments may contain analytes and reagents that will react together during stacking and en route to the detector (see J. Ruzicka et al, Analytical Chemistry (American Chemical Society), 1990, vol. 62 p.1861; and M. Guzman et al, Talanta, (Pergamon Press), 1993, vol. 40 pp.81–87). Published systems involve use of a single pump (syringe or peristaltic) and a single rotary selection valve having as many as ten ports arranged around a central orifice connected to coil and then to pump. The valve is controlled by an electronic actuator, with the better actuators being able to move through the ports in both clockwise and counter-clockwise directions. Only one port is accessed at any time. When compared to flow injection analysis, sequential injection analysis systems have the advantage of being able to access an increased number of solutions with just one pump.

The PASS (Purdue Automated Synthesis System) conventional robotic system which uses two robots in series undertakes sample preparation or reaction which includes the addition of reagents, mixing and the like at a first robot and then conveys the prepared sample to a second system which performs analytical functions such as presentation of the prepared sample to a gas chromotograph (GC). In the PASS system, the means of transfer between the two robot systems is via a small train.

However, prior art apparatus is different and inferior to apparatus according to the present invention in that the prior art apparatus does not permit the following.

a. It does not facilitate overlaying of zones which have been stacked in separate coils.

b. It does not facilitate any of the modes of operation that require more than one port to be open simultaneously in that the rotary valve is limited such that only one port may be accessed at any one time.

c. It does not facilitate separate simultaneous reaction of multiple stacked zones for example, in parallel holding coils.

d. It does not facilitate any mode that requires rapid alternation between ports in that the rotary design of the valve requires that ports must be accessed in order.

e. It does not facilitate solvent modulation.

f. It does not facilitate continuously variable solvent compositions.

g. Use of a single pump does not facilitate preparation and use of linear concentration gradients by synchronous variations of flow rates. Any concentration gradients produced are only by means of mixing chambers or dispersion.

h. It does not facilitate air-segmented continuous flow analysis.

i. The solution—handling parts of the apparatus of the prior art do not constitute a flow analysis network, since they work in isolation.

SUMMARY OF THE INVENTION

It is an object of the present invention to provide an extensible class of flow robotic instruments herein termed as "flow analysis networks".

Thus, the flow analysis network apparatus of the present invention provides for the transfer of gaseous or liquid fluids from one component to another component of the apparatus in a flexible, programmable manner similar in principle to the transfer of data between electronic subsystems of a network in microcomputing. The present apparatus allows of the sequential addition of apparatus components in a manner that the parts constitute a synergistically operating combination in the tasks of analysis, sample preparation or synthesis. All the process operations can be performed in automated, flexible sequences and under computer control. The operating mode of the invention is user-programmable and is determined by easy-to-use multi-purpose software and, as such, it is an example of soft automation. This is different from traditional hard automation systems which support a single analytical technique or method using single-purpose hardware and software. The segments of fluid may be selected and/or reacted in random access fashion as opposed to in sequence and introduced into fluid streams in random access fashion as opposed to sequentially.

Embodiments of the apparatus and process of the invention, by reason of their inherent flexibility and high degree of computer control, which include sufficient valves and pumps, may also be used to implement any of the flow analysis techniques presently known as sequential injection analysis, flow injection analysis, merging zones flow injection analysis, solvent extraction flow injection analysis, air-segmented continuous flow analysis, batch injection analysis, and related less widely practiced techniques.

Accordingly, in one aspect, the invention provides a flow analysis network apparatus comprising

- a multiport valve means having a plurality of ports; each of said ports adapted to receive therethrough a selected fluid;
- fluid stacking means wherein a plurality of selected fluids may be stacked in predetermined order in communication with said valve means;
- fluid contacting zones wherein at least two of said selected fluids may make contact or combine one fluid with another fluid;
- conduit means in communication with said ports and said fluid stacking means, whereby selected fluids may be selectively transferred between said ports and said fluid stacking means;
- pump means for effecting passage of said selected fluids through said valve means, said conduit means and said fluid stacking means;
- control means to selectively control passage of selected fluids though said valve means;
- port selection means associated with said control means;
- sensing means associated with said control means and said valve means;

the improvement comprising said fluid stacking means comprising at least a first fluid stacking means wherein a first plurality of said zones of selected fluids may be stacked in predetermined order and a second fluid stacking means wherein a second plurality of said zones of selected fluids may be stacked in pre-determined order.

By the term "selected fluid" as used in this specification and claims is meant a desired same or different fluid as selected by the control means for passage through the conduit means, valves and ports.

The components of the apparatus may be in direct communication one with another or may communicate one component with another through a third or more components.

The fluid stacking means may comprise a fluid contact zone.

Preferably, a network as defined hereinabove further comprises a third fluid contact zone wherein selected fluids from at least said first plurality of zones and said second plurality of zones may make contact.

A network as defined hereinabove may constitute apparatus wherein said pump means comprises at least a first pump for effecting passage of said selected fluids through said first fluid contact zone and a second pump for effecting passage of said selected fluids through said second fluid contact zone. Further, said conduit means may be in communication with each of said ports to allow selected fluids to be selectively transferred between at least two of said ports.

Thus, in contrast to conventional sequential injection systems, where rotary valves are de facto, the apparatus of the present invention has one or more random access multiport valve hubs, each having a plurality of valves to control fluid flows. The plurality of ports may receive the fluids, simultaneously, by means of the independent control of opening and closing of individual ports through use of concealed port mini-valves. A determined plurality of ports may be of the same number or a different number. Thus the multiport valve is adapted to receive, simultaneously, therethrough, selected fluid flows from at least two of the ports.

In a further aspect the invention provides a flow analysis network apparatus comprising

- a first multiport valve means having a plurality of first ports;
- a second multiport valve means having a plurality of second ports;
- each of said first ports and said second ports adapted to receive therethrough a selected fluid;
- fluid stacking means wherein a first plurality of selected fluids may be stacked in predetermined order in communication with said first multiport valve means;
- first conduit means in communication with said first ports and said second ports, whereby selected fluids may be selectively transferred to selected first ports and selected second ports;
- first control means associated with said first valve means to selectively control passage of selected fluids therethrough;
- second control means associated with said second valve means to selectively control passage of selected fluids therethrough;
- pump means for effecting passage of said selected fluids through said conduit means;
- sensing means associated with said first and second control means; and
- selection means associated with said first and second control means.

In a yet further aspect the invention provides a flow analysis network apparatus as hereinabove defined further comprising

- a third multiport valve means having a plurality of third ports, each of said third ports being adapted to receive therethrough a selected fluid and third fluid stacking means wherein a third plurality of selected fluids may be stacked in predetermined order in communication with said third valve means;
- second conduit means in communication with said pump means, said first ports, said second ports and said third ports, whereby selected fluids may be selectively transferred to a selected first port, selected second port and selected third port; and
- third control means associated with said sensing means, said selection means and said third valve means to selectively control passage of selected fluids through said third valve means.

The apparatus may, optimally, comprise wherein said

- first multiport valve means, said second multiport valve means and said third multiport valve means are in direct communication one with each other through said first conduit means and said second conduit means.

In a still yet further aspect the invention provides a flow analysis network apparatus comprising a plurality of multiport valve means wherein each of said valve means has a determined plurality of ports adapted to receive selected fluids therethrough and fluid stacking means wherein a plurality of selected fluids may be stacked in predetermined order in communication with said valve means;

- conduit means in communication with at least two of said multiport valves whereby selected fluids may be selectively transferred to selected ports of said at least two of said multiport valves;
- control means associated with said valve means to selectively control passage of selected fluids therethrough;
- pump means for effecting passage of said selected fluids through said conduit means;
- sensing means associated with said control means; and
- selection means associated with said control means.

Embodiments of the invention may be configured to perform, inter alia, as an air-segmented flow analyzer, a flow injection analyzer, a sequential injection analyzer, a batch injection analyzer, a full flow analysis network having many of the properties of co-operant multi-hub robotic systems, a chemical analyzer in a laboratory, a "roll-up" analyzer for industrial process diagnostics, an industrial process monitoring system capable of unattended operation, an environmental monitoring system capable of remote deployment and unattended operation, and a bench micro-scale automated synthesis system.

The apparatus of the invention may operate in either a continuous manner or an intermittent manner.

The process of the invention may comprise, inter alia, one or more reagent addition steps, one or more solvent extraction steps, one or more sorbent extraction steps, one or more digestive steps, one or more gas diffusion steps, one or more dilution steps, one or more heating steps, one or more distillation steps, one or more irradiating steps, one or more sonicating steps or one or more reactor cells.

The invention provides a system comprised of components which work together, both simultaneously and in sequence under synchronized computer control to achieve the requested fluid robotics operations. It provides means to stack, mix and move around segments of fluids, including reagents, samples, carrier solutions and air through a network of tubing in a highly reproducible manner and with highly accurate timing.

The apparatus and process of the invention by virtue of versatile hardware and intelligent software, can accommodate multiple methodologies, such as chemical, biochemical and other analytical methods, at one time. In one embodiment, the system is designed specifically to access methodologies in a random manner rather than sequentially or in parallel.

The system may be reconfigurable, via software and support both existing standard methods of analysis and rapid development and implementation of new methods. The system in an alternative embodiment can self-calibrate at predetermined times or in response to prompts from the user or from internal diagnostic routines. It can use, as its means of self-calibration, any of the following, namely, pre-prepared solutions of known concentration, physical dilutions of standard solutions carried out in an automated fashion by the instrument, or dispersion profiles of standard solutions of known concentration.

The control means of use in the invention as hereinabove defined for the multiport valve hubs is such that simultaneous flow through more that one port may be undertaken. This is contrary to conventional sequential injection systems where rotary valves restrict operation such that only one port may be open at one time.

In one embodiment of the invention the apparatus can modify the composition of its carrier solvent stream and reagent streams by rapid alternation or sequencing of the opening of random access valve ports.

In a further embodiment, the apparatus provides intelligent sample diagnostics. It incorporates within its operating software, routines which allow real-time estimation of data quality, as well as quantitation. These quality routines involve estimation of differences in peak shape relative to a preferred optimal peak shape. The smaller these differences, the better the quality assigned to the peak.

The apparatus may include software routines that can infer from readings obtained from sensors, the presence of difficult samples, including those which have an analyte concentration outside the boundaries of the normal working range and those which have an abnormal pH or background absorbance. The apparatus control software may allow the system to automatically reconfigure its operation in real-time so as to handle these difficult samples. The system software can provide intelligent instrument diagnostics. Examples of detectable problems include (1) progressively worsening peak shape quality, coupled with excessive tailing, indicates precipitate build-up caused by suboptimal chemical conditions and/or abnormal samples, (2) if a flow rate sensor indicates that no flow is occurring in a line where there should be a flow, the instrument will conclude that either (i) a large leak occurred, (ii) a pump had malfunctioned, (iii) a valve had not opened, or (iv) there was a problem with the sensor itself.

In a further embodiment, the apparatus can carry out diagnostic tests, such as for example, diverting another fluid flow across the same sensor to more closely identify a problem and then recommend remedial action. Included in the software and used by the diagnostics routines, is the service record of each component of the analyzer. The system software may include control routines that can self-optimize analytical methods to find the flow rates, solution volumes, flow paths and timing combinations which give the most preferred values of objective functions specified by the user. Such functions may include analytical detection limit, analytical sensitivity, cost per analysis, time per analysis and combinations thereof.

The apparatus can be adapted to be used for kinetic analyses where the measured quantity associated with analyte concentration is a rate of change of response at the detector(s), rather than a steady-state signal.

In further embodiments, the apparatus can continue operations using back-up routines, while certain types of maintenance are performed, and can provide limited self-repair capacity. For chemical problems, such as precipitate formation, the analyzer has the capacity to send acid or base streams to the problem site and attempt to "repair itself" by dissolution of the precipitate. It may in a further embodiment, provide limited fault-tolerant operation. When implemented with large numbers of random access valves which is an inherent redundancy of connections, the apparatus of the invention is able to re-route streams to maintain operation whilst maintenance is ordered. The resultant decrease in "down-time" has significant economic advantages in the laboratory and safety advantages in process situations.

BRIEF DESCRIPTION OF THE DRAWINGS

In order that the invention may be better understood preferred embodiments will now be described by way of example only, with reference to the accompanying drawings, wherein:

FIG. 2(A) represents a diagrammatic enlargement, in part section, of a coil of FIG. 2;

FIG. 6 represents diagrammatic sketches of embodiments of components and designs of use in the practice of the invention as follows: FIG. 6(a) a rotary valve used in conventional sequential injection analysis; FIG. 6(b) a random access valve hub of star design, wherein one port may be opened to allow fluid to flow to or from the central access port connected to an external conduit; FIG. 6(c) a random access valve hub of star design similar to FIG. 6(b), but wherein more than one port may be opened to allow fluid to flow to or from the central access port connected to an external conduit; FIG. 6(d) a random access valve hub of star design similar to FIG. 6(c), but wherein more than one port may be opened to allow fluid to flow, via a shared central confluence, out via another port connected to an external conduit; FIG. 6(e) a linear random access design, wherein more than one port may be opened to allow fluid to flow to or from a common access conduit connected to an external conduit, with all ports of the same side; FIG. 6(f) a design, similar to FIG. 6(e) with ports staggered on both sides to allow for a shorter common conduit; and as FIG. 6(g) a design similar to FIG. 6(f) but herein the ports may be on multiple sides to allow an even shorter internal conduit and injection of different fluids from different ports at essentially the same location and with minimal dead volume;

FIGS. 6(h), 6(i) and 6(j) are side views of FIGS. 6(e), 6(f) and 6(g), respectively;

FIG. 7(C) represents a further embodiment of an advanced operation mode for a flow network apparatus with at least three pumping systems;

DETAILED DESCRIPTION OF PREFERRED EMBODIMENTS

Figure 1:
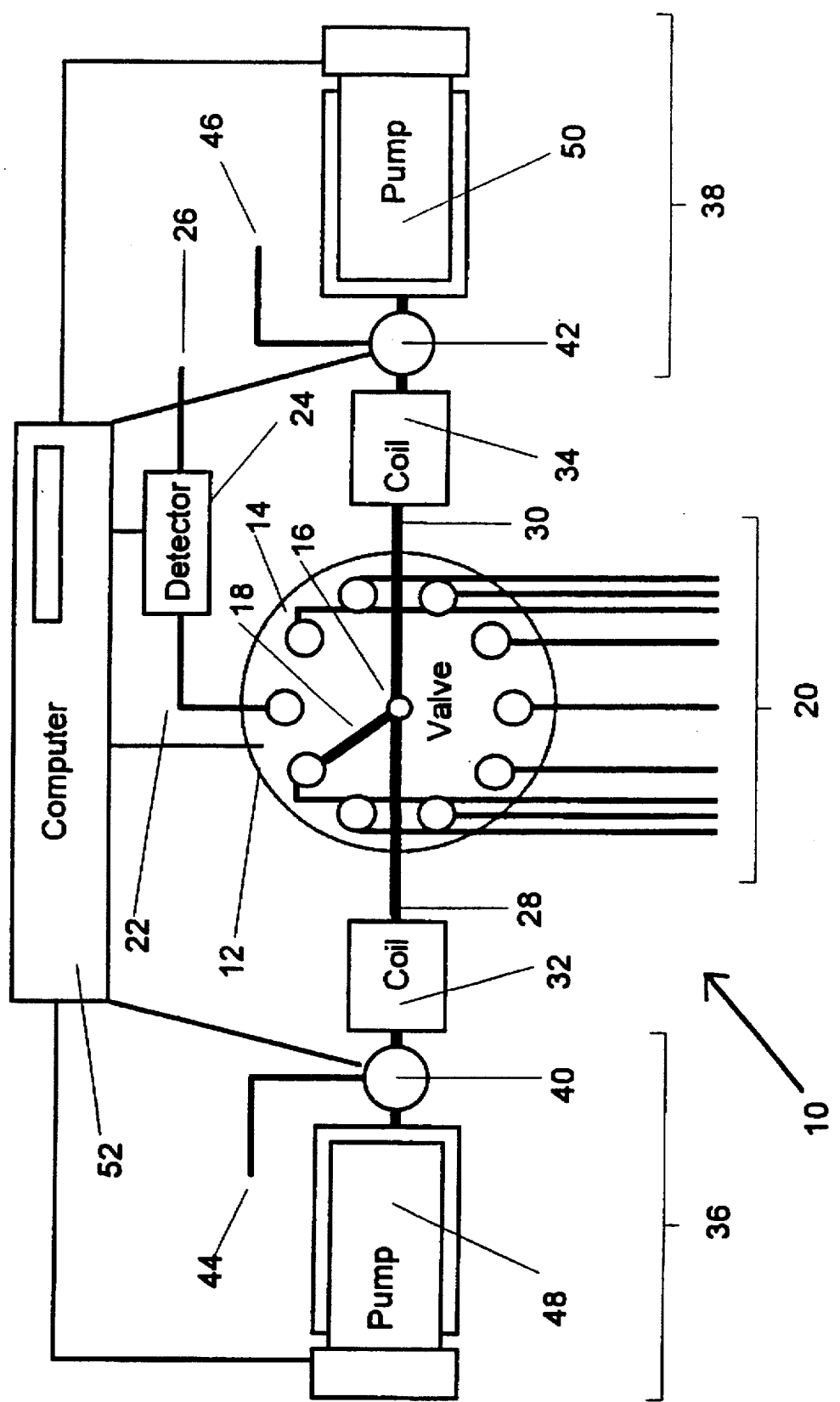
FIG. 1 represents a diagrammatic layout of a flow analysis network apparatus of one embodiment according to the invention.

FIG. 1 shows generally as 10, a flow analysis network apparatus configured as a cooperant sequential injection analyzer having the minimum configuration needed to execute the experimental sequences shown hereinafter with reference to FIGS. 7A and 7B. Apparatus 10 comprises two cooperant bi-directional pumps, two stacking coils and one random-access stream selection hub, wherein various fluids and a detector are arranged around the hub and the active components of the system are controlled by a computer.

FIG. 1 shows a valve hub 12 having a plurality of ports 14, totalling ten in this embodiment, whereby various fluids or system components can be accessed. Valve hub 12 has a central common access port 16 and a selector mechanism 18 whereby one or more of ports 14, optionally simultaneously, have access to central access port 16. Valve hub 12 is completed by small bore inert conduit tubing from each of ports 14 to constitute value hub system shown generally as 20, which conduit leads to vessels containing fluids, such as for example, sample, reagents, wash and other chemical or biochemical fluids or to detectors or to waste container or stream or to other sample processing apparatus. Any of the aforesaid may be attached to each of ports 14. As an example, one such conduit 22 is connected by a tubing of diameter and length selected such that it does not adversely affect dispersion of overlapped zones, to a detector 24, and thence to a waste container 26. In the instance that detector 24 may destroy the sample, as would be the case if it were a flame atomic absorption spectrophotometer, there would be no waste container 26. Common access port 16 is connected via conduit to tubing 28 and 30 to stacking coils 32 and 34 respectively, and pumping systems 36 and 38, respectively, first pumping system 36 is comprised of a three-way valve 40 by which wash or carrier solution can be introduced from a vessel (not shown) via tubing 44. For those pump systems having valves which allow connection of wash/conduit carrier 44 to coil 32, the wash/carrier solution may be pulled under negative pressure by a syringe pump 50 of second pump system 38. Second pump system 38 is comprised of a three way valve 42 by which wash or carrier solution can be introduced to prime pump 50. The wash or carrier solution is introduced from a vessel (not shown) via a conduit tubing 46. For valves which allow connection of wash/carrier conduit 46 to coil 34, the wash/carrier solution may be pulled under negative pressure by first pump 48. The active components of the system, namely, pumps 48, 50, priming valves 40, 42, valve hub system 20 and detector 24 are controlled by control computer 52 via appropriate analog and/or digital communications protocols. Coils 32, 34 are termed "coils" because in normal practice coiled tubing of length, for example, 1–5 meters and internal diameter 0.5–0.8 mm is used in a tightly coiled or knotted fashion so as to decrease longitudinal dispersion. Use of the term "coil" is common practice in flow analysis, and should not be taken to preclude use of straight tubing, knotted tubing, tubing containing beads or other dispersion modifying aids, reactive materials such as particles of solid phase catalysts, or even mixing chambers. The coils themselves may be individually temperature controlled, either by means of control computer 52 or auxiliary systems (not shown). The contents of the coils may also be subjected to external excitation such as ultraviolet light, ultrasound, heat, radiation or microwave energy, with the source of these exciting phenomena being either controlled by control computer 52 or by auxiliary systems (not shown).

In the embodiment shown in FIG. 1 as a laboratory instrument the network apparatus is capable of performing multiple chemical reactions in random or sequential fashion, and either continuously or intermittently. This embodiment represents an instrument which provides intelligent, random, intermittent analysis of fluids. Specifically, it addresses the situation where, for example, 64 analyses for each of 6 or 7 analytes are required per day, in batches of four, collected every three hours, and where the requirement for analyses is immediate. In such a situation, there are insufficient numbers of each analysis to merit a large-scale parallel air-segmented continuous flow analyzer, manual reconfiguring of a single flow injection analysis system is impractical, and individual analyzers for each chemical reaction are too expensive and would be under utilized.

The following provides some examples of the operation of the apparatus of FIG. 1.

It is normal practice to prime the system with appropriate carrier fluids prior to use. The process will differ depending on whether syringe or peristaltic pumps are used.

Syringe Pumps. Small syringe volumes (5 ml or less) are to be preferred on grounds of precision and accuracy. Syringe pumps are typically driven by stepper motors—each "step" taken is as a result of an electronic control pulse received by the syringe. The full "throw" of the syringe (e.g. from fully reversed to fully forward positions, corresponds to a known number of pulses and to delivery of the full volume of the syringe. Therefore, use of a small syringe corresponds to delivery of a smaller volume of fluid per step pulse and, therefore, to more precise flow control. For any syringe pump which uses gearing systems and a motor drive, the flow precision is a function of the ability of the drive to stop and start. However, one disadvantage of smaller syringe sizes is that priming operations may require multiple fillings of the syringe, as may entrainment of volumes of solutions larger than about half of the volume of the syringe in the holding coils.

Syringe pumps are normally mounted vertically with the open end of the syringe upwards. The intent of this is to cause the carrier fluid, usually a liquid, to fall to the bottom of the syringe and any air, which is less dense, to be readily expelled from the top of the syringe during normal operation. This is important since air is more compressible than liquids and, therefore, would contribute to decreased control over desired flow rates. Generally, in ideal operation as a liquid-phase sequential injection analysis system, there should be no air entrapped in the analyzer. Gas bubbles may also form at the interface between two dissimilar liquids under negative pressures, or arise as a result of chemical reaction or interaction, or come out of solution as a result of change in temperature or other solution properties, or enter the system through lines which lose contact with their filler solutions, e.g. when a solution reservoir is exhausted, or may enter the system through imperfect connections, especially under negative pressures caused by "sucking" pumps. With the exception of any air entering at valves 40, 42, these bubbles would normally not enter the pump and would be confined to the rest of the manifold and expelled from it during normal operation of the pump.

To prime the side of the system made up of conduit 28, coil 32 and valve 40, the following instructional steps are follows. Open valve 40 such that pump 48 is connected to the wash/carrier solution, and coil 32 is isolated, e.g. not connected to pump 48. Cause pump 48 to pull fluid, usually a liquid, from stream to wash/carrier 48 through valve 40. Switch valve 40 to connect pump 48 to coil 32 and switch valve hub 12 to select a port 14 which is connected to waste. This may include a line 26 that includes within it detector or sensor 24, or it may be a line 20 that is connected directly to waste. To prime the second side of the system, which is made up of conduit 30, coil 34 and valve 42, stream to wash/carrier solution 46 and pump 50, undertake the same operations as for the first side of the system. To prime remaining lines 20 attached to valve hub 12, sequentially select each port 14 and, using either or both pumps, draw sufficient fluid present in fill tube 20 for example into the valve hub, conduit and coil such that the desired fluid at the end of tube 20 passes through port 14 and reaches valve hub 12. Then, select a port 14 that is connected to waste and, using the same pump(s) push the unwanted fluid that passed into the conduits and coils out through the selected port and to waste. In the event that the waste port selected is as shown 26, and, thus, includes detector 24, detector 24 may be used to determine that all of the unwanted fluid has, indeed, been expelled from this part of the system. This action should be repeated until all unwanted fluid, including air microbubbles in liquid streams, has been expelled from the system. If the syringe volume is not significantly larger than the total internal volume of the system, this may require several strokes of the syringe to accomplish.

It should be noted that valves 40, 42 may have more than the three connections shown. A valve with four ports, for example, would allow the pump to select from two alternate wash/carrier solutions. These might include deionized water for operating purposes, and dilute nitric acid with surfactant for cleaning purposes as described hereinbelow. Another alternative embodiment would include use of a four or more port mini-valve to prepare a carrier or wash solution comprised of varying amounts of two or more fluids. An example of this would be ethanol/water mixtures which are needed by some analytical methods where the reagents or products are only sparingly soluble in deionized water but are much more soluble in alcohols. It is within the scope of the present invention that the flow analysis network embraces embodiments which include more than one fluid within a system. These are for gas phase sampling, air-segmented continuous flow analysis, solvent segmented continuous flow analysis, automated solvent extraction, solvent composition modification and solvent composition modulation.

Peristaltic pumps. A peristaltic pump pulls fluid from one side and pushes it to the other by means of a set of rollers and compressible pump tubing. Such pumps are bi-directional. They are by far the most common form of fluid propulsion used in air-segmented continuous flow analysis and flow injection analysis.

To prime a system using a peristaltic pump is a matter of connecting the inflow to a source of wash/carrier solution, and the outflow to coil 32, and switching valve hub 12 to access a port 14 that is connected to waste. Flow is then allowed to occur unidirectionally through peristaltic pump 48, coil 32, conduit 28, central port 16, internal conduit 18, selected port 14 and, as before, to waste. Priming of second peristaltic pump 50 is the same as for first pump 48. Priming of other lines 20 requires bi-directional flow and follows the same principal as for syringe pumps. Valve 40 may be placed either upstream or downstream of the peristaltic pumps to allow the pumps to access more than one fluid. Such a system and operation of the present invention is novel in air segmented continuous flow analysis, solvent extraction, gas sampling, solvent composition manipulation or solvent composition modulation.

Cleaning the system. After use, it is normal practice to effect automated cleaning of the system. Cleaning follows exactly the same protocol as for priming and employs solutions containing dilute acids or organic solvents and surfactants. The system is refilled, e.g. re-primed with deionized water after the cleaning solution has been expelled.

Operation modes. Specific modes of operation of the device shown in FIG. 1 are now discussed.

(A) A first mode of operation is an example of a merging zones form of sequential injection analysis which involves a simultaneous use of both pumps moving in the same direction. The system is first primed and each pump 48, 50 is left in position such that it can draw further fluid back into itself or back through itself in the case of peristaltic pumps. At this stage, ideally the pump should not be empty but should be about half full of wash, since later it will need to deliver a volume of reacting solutions to detector 24. Valve 40 is switched to connect pump 48 to coil 32, and valve hub 12 is switched to allow central port 16 to access a port 14 to which a sample line is attached.

Ensuring fresh sample. So as to ensure that fresh sample is used, and not "old" sample fluid that had been left standing in line 20, pump 48 is operated such that a volume of sample is brought back through conduit 28 and into coil 32. Valve hub 12 then switches to select an alternative port 14 that is connected to waste and the direction of pump 48 is reversed to expel the "old" sample solution to waste. This process may be repeated several times until a sufficient volume of "old" sample or perhaps as large as five times the volume of line 20 has been expelled to ensure that the sample to be reacted is current. This part of the process, e.g. a "re-priming" with current sample, is particularly important where the sample may have been taken from a connecting tube interfaced to an industrial process, the progress of which, or the present value of a chemical concentration within which, is an object of prime interest.

Facilitating chemical reaction. Having established that the sample which can enter the valve is current, pump 48 is stopped while valve hub 12 again selects the port 14 to which sample is connected. Pump 48 then draws back into conduit 28 and, depending on volume, coil 32, a volume of sample solution for analysis. This may be as little as 10 µl or as much as 250 µl, with typical volumes being around 50 µl. Pump 48 is then stopped while valve hub 12 selects another port 14 attached to a standard solution containing a known concentration of the analyte to be determined, preferably in the same matrix as the sample contains. Pump 48 then draws back a volume of standard solution. Again, this may be as little as 10 µl or as much as 250 µl, with typical volumes being around 50 µl. Pump 40 then stops and waits for actions by second pump 50. Valve hub 12 selects a port 14 which is already primed and connected to a reagent suitable for reaction with analyte(s) in the sample and standard solutions. Pump 50 then draws back a volume of reagent into conduit 30 and if the column is large enough into coil 34 and stops. Assuming that one wished to achieve exactly the overlap shown in FIG. 7(A), valve hub 12 would then select a port 14 connected to wash, and draw back into conduit 30—and possibly coil 34 a small volume of wash so as to adjust the position of the reagent zone so that in the next step it will overlay with both the sample and standard zones already stacked up by first pump 48. Valve hub 12 then selects the port 14 attached to conduit 22 leading to detector 24. Each of pumps 48, 50 then pushes the solutions entrained in their respective conduits through central port 16 and into conduit 22 leading to detector 24. As the two streams meet from conduit 28 and conduit 30 at central access port 16, first there will be overlap of standard (last in—first out and wash, then standard and reagent (reaction starts), then sample and reagent (reaction starts), and finally sample and wash. The reacting mixtures proceed through conduit 22 to detector 24, at which the contents of the stream are sensed. As shown in FIG. 7(A), this results in seven different types of analytical information, namely, with a photometer as detector, the absorbance signals detected from:—the initial baseline, standard background, product of standard and reagent, product of mix of standard, sample and reagent, product from sample and reagent, and sample background, and return to baseline. After expulsion of the mixed solutions from the system, the system may be returned to its starting configurations. To do this, valve hub 12 is used to access a port 14 connected to a wash solution and pumps 48, 50 draw sufficient wash solution to return them to their starting positions.

A vast number of variations on this theme are possible using one, two, or more stacked zones within each coil. While the overlap pattern achieved is as shown in FIG. 7(A), extension of the principle to the more complicated case shown in FIG. 7(B) is straightforward, in that it requires only further manipulations involving valve hub 12 and second pump 50. Indeed, the first pump can achieve any of the following single-zone arrangements:

Wash.-Reagent-Wash,
Wash.-Sample-Wash,
Wash.-Standard-Wash,
Wash.-Reagent-Wash,
Wash.-Buffer-Wash,
Wash.-Modifier-Wash, and
Wash.-Solvent-Wash.

Modifiers include masking agents, ionic strength modifiers, and any other chemical that the operator may wish to utilize. It can also achieve all two-zone combinations, including:

Wash.-Sample #1-Standard #1-Wash,
Wash.-Sample #1-Reagent #1-Wash,
Wash.-Sample #1-Reagent #2-Wash, and
Wash.-Standard #2-Reagent #2-Wash, etc.

All three-zone and greater combinations are also possible, including:

Wash.-Reagent #1-Sample #1-Reagent #2-Wash, and
Wash.-Reagent #1-Standard #1-Standard #2-Reagent #2, etc.

Further options that may be present or absent from any combination include:

The overlap of the stacked zones may be varied via timing delay of operation of one of the two pumps (see discussion of FIGS. 7(A), (B), (C) and (D) below hereinafter).

Overlap may be further modified by operating the pumps either synchronously or in alternating fashion.

Detection may be with the fluid in the detector stopped or with the fluid in the detector flowing.

Detection may be of a single signal parameter, or of multiple parameters, for example, via use of a diode array spectrophotometer, which measures the absorbance of light at multiple wavelengths simultaneously.

The manifold may be of open tubular design, or otherwise.

Enhanced mixing may be achieved in vessels attached to a valve hub, by single bead string reactors, mixing chambers, ultrasonic stimulation, or other means.

Flow rates used by the two pumps may be different such that where a low detection limit is required second pump 50 delivers its reagent plug in a manner that maintains the required pattern of overlap but using a much lower flow rate than that used by first pump 48, so as to minimize the diluting effect of adding reagent at the central access point 16. In order to achieve this, whilst maintaining usable dynamic range of the method, and seeking to maintain linear dynamic range of the method, the concentration of the reagent solution used should be raised by the ratio of the flow rates used. Typically, the reagent concentration is calculated on this basis such that it exceeds that required to react with all of the analyte present, even at the highest likely analyte concentration. Thus, if pump one 48 and pump two 50 were initially both to use flow rates of 1 ml/min, and in the revised mode pump two 50 would be used at 0.2 ml/min, the reagent concentration attached to selected port 14 should have been raised by a factor of 1.0/0.2=5, so as to maintain the same analyte to reagent ratio at the central access port and en route to the detector. Dilution of analyte by the stream containing the reagent would be reduced from 100% to just 20%, with a resultant improvement in detection limit. If pump two 50 were operated using a faster flow rate than pump one 48, yet maintaining the overlap stipulated in FIG. 8(A), then higher dilution of the sample (analyte) would be achieved. This would be useful for high concentration samples, when a dilution factor of perhaps 5 would allow them to be analyzed using the same method and manifold as samples containing more regular analyte concentrations. Thus, the range of concentrations that the analyzer can determine is essentially programmable via its mode of operation. This increased flexibility adds two orders of magnitude to the analytical capabilities of the instrumentation, relative to conventional sequential injection analysis, flow injection analysis, or air-segmented continuous flow analysis.

Where the reaction between reagent and analyte(s) is slow, more time may be needed to achieve sufficient product formation for sensitive detection. In such cases, the pumps may be stopped to allow reaction within conduit 22 before later restarting them and flowing the reacting/reacted mixture to detector 24 for sensing.

Where the reaction is slow and, possibly, the sample solution may have a variable and unknown background absorbance (which is independent of the analyte concentration within the sample) then kinetic methods may be employed. An example of such a situation would be where one wished to determine caffeine concentration in a variety of commercial soft drinks and where a slow reaction e.g. over in 20–600 seconds is available whereby the caffeine content may be monitored. Each drink has a different colour, and different colour intensity. To measure their caffeine content, the first streams are best arranged such that the standard and sample zones are aspirated into coil 32 as standard first, sample second. The second pump 50 aspirates reagent and wash as before. Conduit 22 between valve hub 12 and detector 24 would be very short, to limit dispersion. On merging of the streams from the first and second conduits 28, 30 the reacting mixture is transported directly into the flow-cell of the detector, and the pumps are stopped. The initial absorbance read by detector 24 will be due to the natural absorbance of the sample solution, plus a contribution from any reaction that occurred in the short time it took for the mixture to pass from the central access port 16 to detector 24 through conduit 22. The absorbance will continue to increase as more of the product of reaction of caffeine with reagent is formed. The rate of formation of the colored product, quantified as the slope of the absorbance vs. time curve, is used to infer the concentration of caffeine and is independent of the sample background absorbance. On restarting the pump, the reacted zone of standard and reagent can be measured as it passes through the detector, again providing for within-run standardization of the analytical method.

The aforesaid discussion refer specifically to situations wherein a sample solution contains some analytes which react with a reagent to form a colored product which is detected by a spectrophotometer. An alternative situation is where the reagent itself is highly absorbing and reaction with analyte results in a measurable decrease in that absorbance. Examples of this are the very rapid reaction of chlorine dioxide with the dyestuff Lissamine Green B at pH 9.4, and the somewhat slower reaction of hydrogen peroxide with Patent Blue Violet. A second alternative arises where the sample solution contains a highly absorbing analyte which itself is decolorized in reproducible and quantitative manner by reaction with the reagents provided. An example of this is permanganate ion.

(B) A second specific mode of operation involves simultaneous use of both pumps, working in opposite directions to facilitate a similar overlay of e.g. a reagent solution onto a stacked set of zones of sample solution and standard(s) solutions. In this, a system as shown in FIG. 1 is first primed. The first pump 48 then stacks up zones of sample and reagent as detailed in the first embodiment. However, second pump 50 does not stack up zones of reagent and wash. Rather, both pumps 48,50 are stopped while valve hub 12 selects a port 14 attached to a reagent stream. The first pump 48 pushes the stacked zones of sample and standard(s) solutions out of coil 32 and through conduit 28 to central access port 16 at a flow rate of perhaps 1 ml/min. Simultaneously, the second pump 50 draws on central access port 16 with a higher flow rate, perhaps of 1.5 ml/min. The end result of this is that the sample and standards zones are transferred into conduit 30 and coil 34 along with reagent that had simultaneously been sucked into the central access port and, hence, contacted with the sample and standard(s) zones by the flow rate difference of 1.5–1.0 ml/min=0.5 ml/min. This achieves essentially the same effect as shown in FIG. 7(A), except that the reagent zone is typically across the whole of the sample and standard(s) zones, and the reacting mixture then resides in coil 34. Both pumps 48 and 50 are then stopped. To facilitate detection, valve hub 12 then selects port 14 connected to conduit 22 and detector 24. Pump 50 then pushes the reacting/reacted zones out of coil 34, through conduit 30, central access port 16, and conduit 22 to detector 24.

Figure 7A:
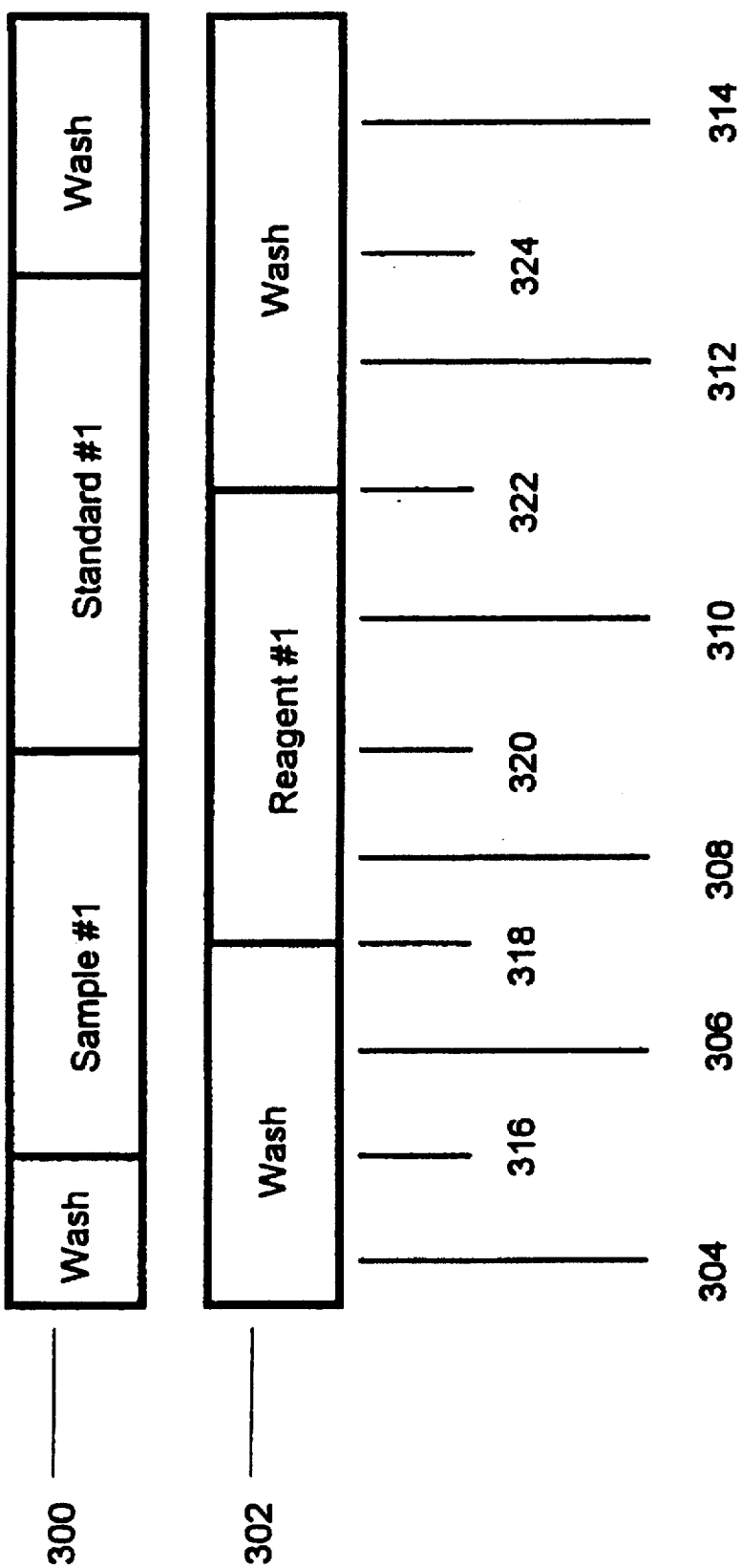
FIG. 7(A) represents a first embodiment of an advanced operation mode for a flow network of the invention with at least two pumping systems wherein a stream containing entrained segments of sample and standard solutions are overlapped with a longer segment of reagent solution.

Alternative switching strategies in which wash and then reagent and then wash are selected from various ports 14 allows the exact equivalent of the overlap shown in FIG. 7(A) to be achieved within coil 34. Volumes of reagent, sample and standard(s) would be expected to be somewhat larger than in the first example, to compensate for additional dispersion during transport. Use of coil 34 for reaction may not be as suitable as the scheme shown in the embodiment for reactions which are slow to go to completion. This is because the zone stacked second in coil 32 travels further within coil 34 than the zone stacked first. The result here is that the zone stacked second has a little longer to react with the reagent and, therefore, could be expected to give a somewhat larger signal than the zone stacked first for the same analyte concentration in each.

Figure 7B:
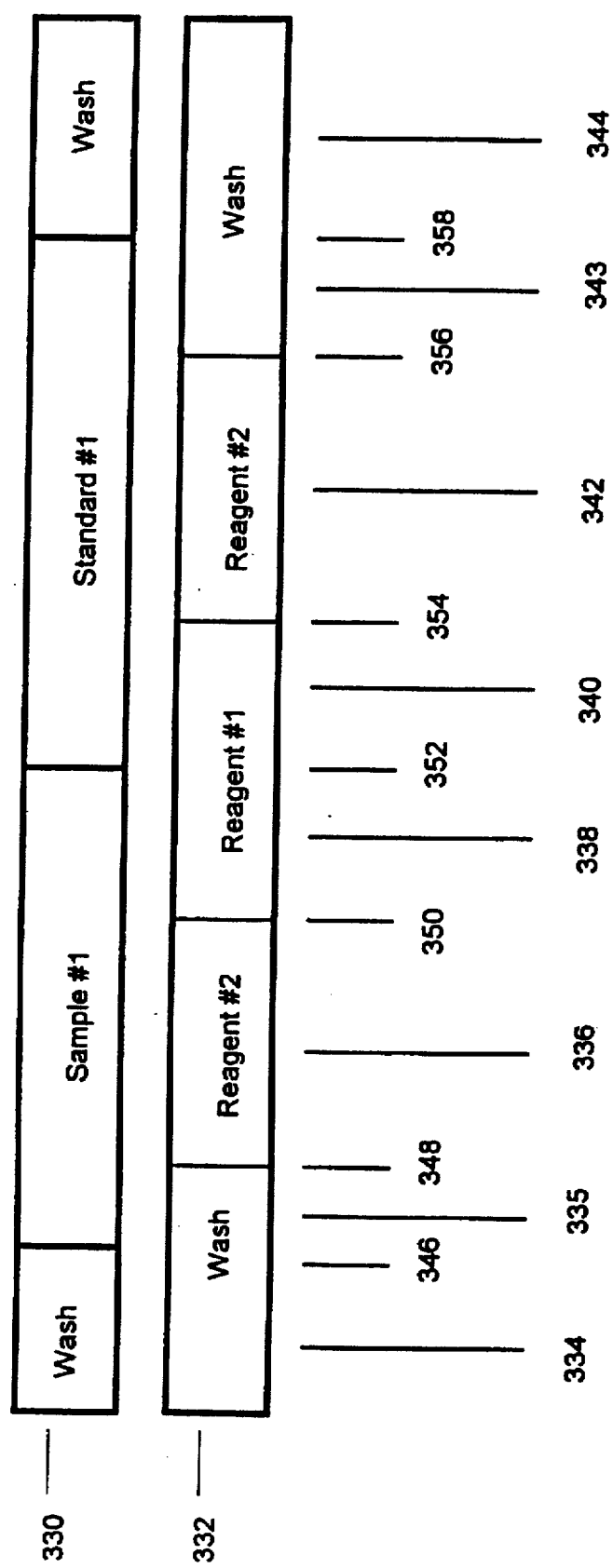
FIG. 7(B) represents a second embodiment of an advanced operation mode for a flow network of the invention with at least two pumping systems wherein a stream containing entrained segments of sample and standard solutions are overlapped with a longer zone containing segments of two reagent solutions.

Extension is the principle to the more complicated case shown in FIG. 7(B) and is straightforward.

(C) A third mode of operation involves a non-simultaneous (intermittent use of the two pumps in either direction to facilitate introduction of e.g. a zone of reagent at one or more predetermined places within a sequence of stacked zones—a technique introduced and termed herein as Automated Random Injection Analysis (ARIA). In this technique, a system as shown in FIG. 1, is first primed. Second pump 50 then draws into conduit 30 and coil 34 a large volume of reagent from one of ports 14 of valve hub 12 sufficient to accomplish more than one analyte determination. Pump 48 then draws into conduit 28 and coil 32 zones of sample and standard(s) solutions from ports 14 of valve hub 12. Valve hub 12 then selects the port 14 connected to conduit 22 and detector 24. Conduit 22 is of sufficient length and design that, as in flow injection analysis, sufficient mixing can occur between zones to allow detection of the products formed by detector 24. Pump 48 then pushes the stacked zones towards valve hub 12 and through into conduit 22 such that, sequentially, the one or more interfaces between zones of sample and standard solutions are placed at central access port 16, and pump 48 is stopped. The second pump 50 then starts in the forward direction to insert or inject a zone of reagent at the interface. The second pump 50 then stops. The first pump 48 then presents the next stacked zone-zone interface to access port 16—at the same time pushing the first reacting mixtures further down conduit 22 and towards detector 24. The first pump stops and the second pump inserts a second zone of reagent. The process continues until all zone-zone interfaces have been treated, whereupon pump one 48 pushes the remaining reacting material to detector 24 and to waste 26. Pump one 48 then returns to its original position by aspirating new wash solution either from mini-valve 40 or a port 14 of valve hub 12 attached to wash. Stacked zones can include zones of wash to separate solutions where needed. This mode of operation has similarity to flow injection analysis in that a zone of one chemical species, here, reagent, is being "injected" into another stream. This multi-zone "injection" is different to that normally obtained in a conventional single-line flow injection manifold but is similar to that which could be obtained at greater complexity by multiple injection valves. It has speed advantages over modes A and B.

A variant on the above procedure involves "partial injection", wherein first pump 48 is not completely stopped during addition of reagent by second pump 50.

A consequent variant involves using pump 50 with a varied flow rate relative to that of pump 48 so as to dynamically change the ratio of fluids delivered by the two pumps to the central access port 16. This is useful, chemically, in studies which seek to determine the stoichiometry of the product formed between analyte A and reagent B (AB, $A_2B$, $AB_2$, etc.). One such method requires a stream comprised entirely of A at one end and entirely of B at the other, with a known, usually linear, gradient of concentrations of A and B in between. Dynamic control of the amount of reagent added is also useful in studies which seek to extend the dynamic range of analytical methods, and in methods themselves with high concentration samples where more reagent may be required.

(D) A fourth mode of operation allows the unit to perform air segmented continuous flow analysis. In this, which could apply to any of the three modes discussed so far, two ports 14 of valve 12 are accessed rapidly in alternating fashion so as to allow the entry of reagent and regularly spaced air bubbles, or sample and regularly spaced air bubbles. This requires a random access valve hub, such as is presented in FIG. 6(b–j), and discussed herein. All other details of operation are the same.

(E) A fifth mode of operation involves an automated dilution step, followed by implementation of any of the overlap protocols illustrated in FIGS. 7(A), 7(B) or discussed hereinabove. To facilitate the automated dilution, valve hub 12 first selects the port 14 which accesses the sample solution. Pump 48 draws a small volume of sample solution e.g. 30–50 µl, depending on the pump repeatability into conduit 28 and then stops. Valve hub 12 then selects a port 14 attached to wash. Pump 48 then draws wash back into the conduit 28, causing the sample solution to reside in coil 32 and then stops. Valve hub 12 then selects a port 14 attached to waste. Pump 48 may move the sample zone backwards and forwards within the coil 32 to cause it to disperse to a greater extent into a greater length of the coil. Pump 48 then expels the majority of the sample through the valve hub 12, to waste, stopping when only the tail of the sample zone remains within the conduit 28. Valve hub 12 then re-selects the port 14 attached to wash and pump 48 then draws back more wash into conduit 28. Valve hub 12 again selects port 14 that connects to waste. Again the remaining sample is encouraged to disperse in the wash solution, by motion backwards and forwards within coil 32. Again, the majority of the sample zone is transferred to waste, leaving only the tail within conduit 28. This process may be repeated several times until the desired degree of dilution has been attained. Finally, the remaining diluted sample zone may be reacted with reagents obtained from the other pump 50, or directly from a port 14 of valve hub 12. The reacting/reacted mixture is then directed to conduit 22 by valve hub 12 and the products are detected by detector 24.

Figure 2:
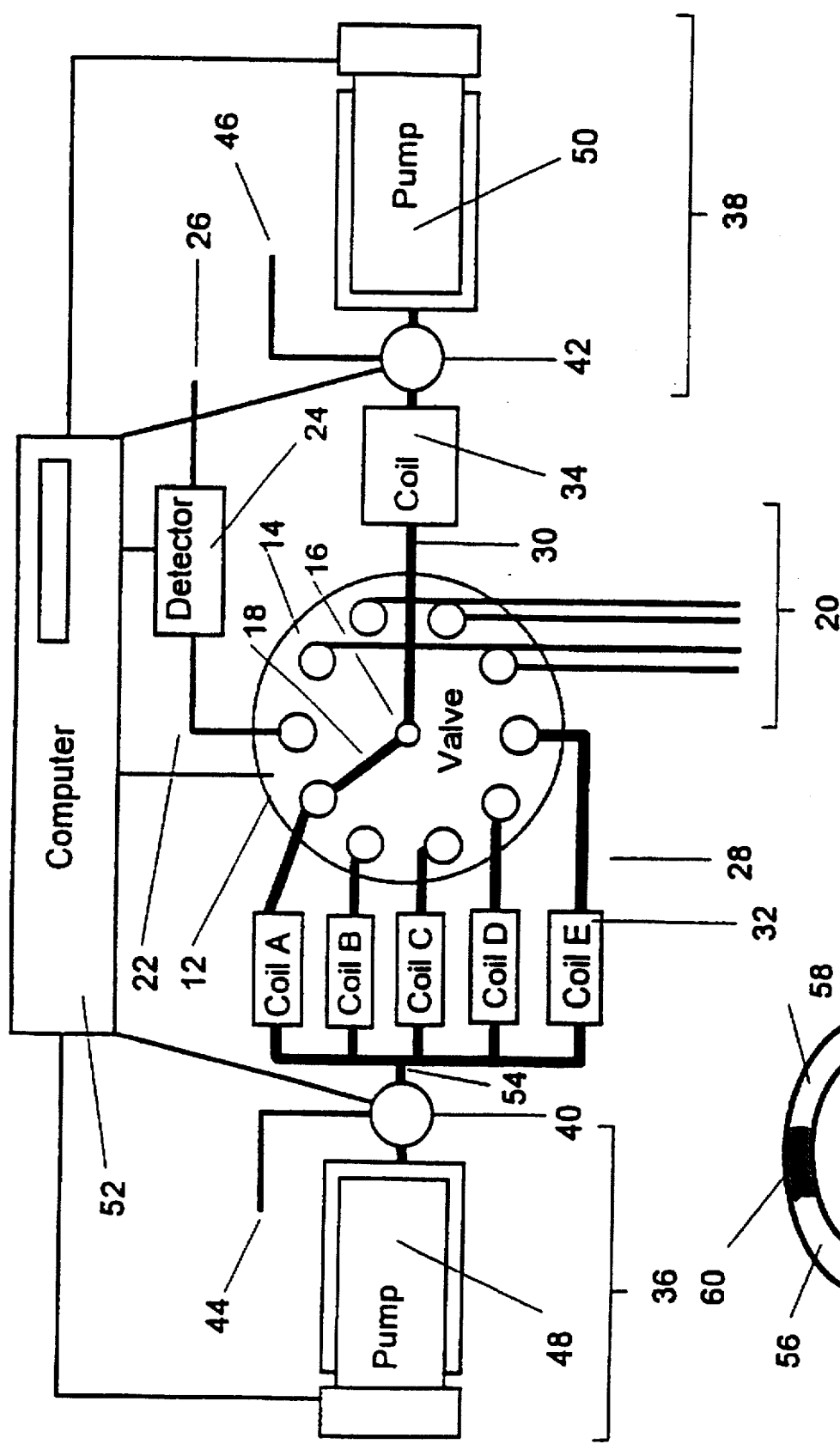
FIG. 2 represents a diagrammatic layout of a flow analysis network apparatus of an alternative embodiment according to the invention.

With reference now to FIG. 2, the apparatus shown comprises two cooperant bi-directional pumps with multiple stacking coils associated with at least one pump and one random-access stream selection hub, wherein various fluids and detectors are arranged around the hub and the active components of the system are controlled by a computer.

One pump can be connected to e.g. five stacking means attached to five ports. The stacking means accessed is determined by the port opened. This is ideal for enzymatic analyses where several reactions can run simultaneously within "parallel" stacking means. As in FIA systems that use parallel coils, this increases reaction time, i.e. the time each sample spends reacting, whilst maintaining sample throughput rate, i.e. the number of samples per hour processed.

FIG. 2 is similar to FIG. 1 but shows a plurality of stacking coils 32(A–E) each attached by a connecting tubing 28 to individual ports 14 and a confluence 54 through which the pump system 36 can push and pull segments of solutions through whichever stacking coil 32 has its associated port 14 in the open state. Stacking coils 32(A–E) are filled and emptied in sequence, thus allowing longer reaction times per sample, whilst maintaining sample throughput rate. Both pumps may be used in the stacking, in any of the ways already discussed. The stacking of zones is illustrated in FIG. 2A with reference to coil E, wherein any coil 32 contains a series of zones and where the boundaries between zones are illustrated by first zone 56, second zone 58 and an interaction region 60.

In the case where zone 56 and zone 58 are immiscible fluids, interaction region 60 represents the interface between them, which can act as a means of passage for substances from zone 56 into zone 58, and vice versa. An example of where this can be used is solvent extraction.

In the case where zone 56 and zone 58 are miscible, the interaction region 60 represents a region of mixing, within which reaction can occur. For example, where zone 56 is sample solution containing analyte, and zone 58 is reagent solution capable of reaction with that analyte, then interaction region 60 represents a third zone which will contain the product of reaction between said analyte and reagent.

An example algorithm for operation of the apparatus of FIG. 2.

STARTUP
PRIME SYSTEM
STACK REAGENT AND SAMPLE 1 INTO COIL A
(or reagent and standard(s), or standard and reagent and sample, etc.)
WAIT FOR×SECONDS
STACK REAGENT AND SAMPLE 2 (etc.) INTO COIL B
WAIT FOR×SECONDS
STACK REAGENT AND SAMPLE 3 (etc.) INTO COIL C
WAIT FOR×SECONDS
STACK REAGENT AND SAMPLE 4 (etc.) INTO COIL D
WAIT FOR×SECONDS
STACK REAGENT AND SAMPLE 5 (etc.) INTO COIL E
OPERATION
EXPEL REACTED MIXTURE 1 (etc.) FROM COIL A TO DETECTOR
STACK REAGENT AND SAMPLE 6 INTO COIL A
EXPEL REACTED MIXTURE 2 (etc.) FROM COIL B TO DETECTOR
STACK REAGENT AND SAMPLE 7 INTO COIL B
EXPEL REACTED MIXTURE 3 (etc.) FROM COIL C TO DETECTOR
STACK REAGENT AND SAMPLE 8 INTO COIL C
EXPEL REACTED MIXTURE 4 (etc.) FROM COIL D TO DETECTOR
STACK REAGENT AND SAMPLE 9 INTO COIL D
EXPEL REACTED MIXTURE 5 (etc.) FROM COIL E TO DETECTOR
STACK REAGENT AND SAMPLE 10 INTO COIL E
EXPEL REACTED MIXTURE 6 (etc.) FROM COIL A TO DETECTOR
STACK REAGENT AND SAMPLE 11 INTO COIL A etc
. . .
CLOSE DOWN
EXPEL REACTED MIXTURE n (etc.) FROM COIL A TO DETECTOR
WAIT FOR×SECONDS
EXPEL REACTED MIXTURE n (etc.) FROM COIL B TO DETECTOR
WAIT FOR×SECONDS
EXPEL REACTED MIXTURE n (etc.) FROM COIL C TO DETECTOR
WAIT FOR×SECONDS
EXPEL REACTED MIXTURE n (etc.) FROM COIL D TO DETECTOR
WAIT FOR×SECONDS
EXPEL REACTED MIXTURE n (etc.) FROM COIL E TO DETECTOR
Wash SYSTEM With reference to FIG. 3, the apparatus comprises two cooperant bi-directional pumps and two stream selection hubs wherein various fluids and detectors are arranged around the hubs. The hubs share at least one common connection to allow the fluids to pass from one hub to another, or for a combination of fluids from both hubs to mix, or for fluids to be passed to one or more detectors. The active components of the system are controlled by a computer.

Figure 3:
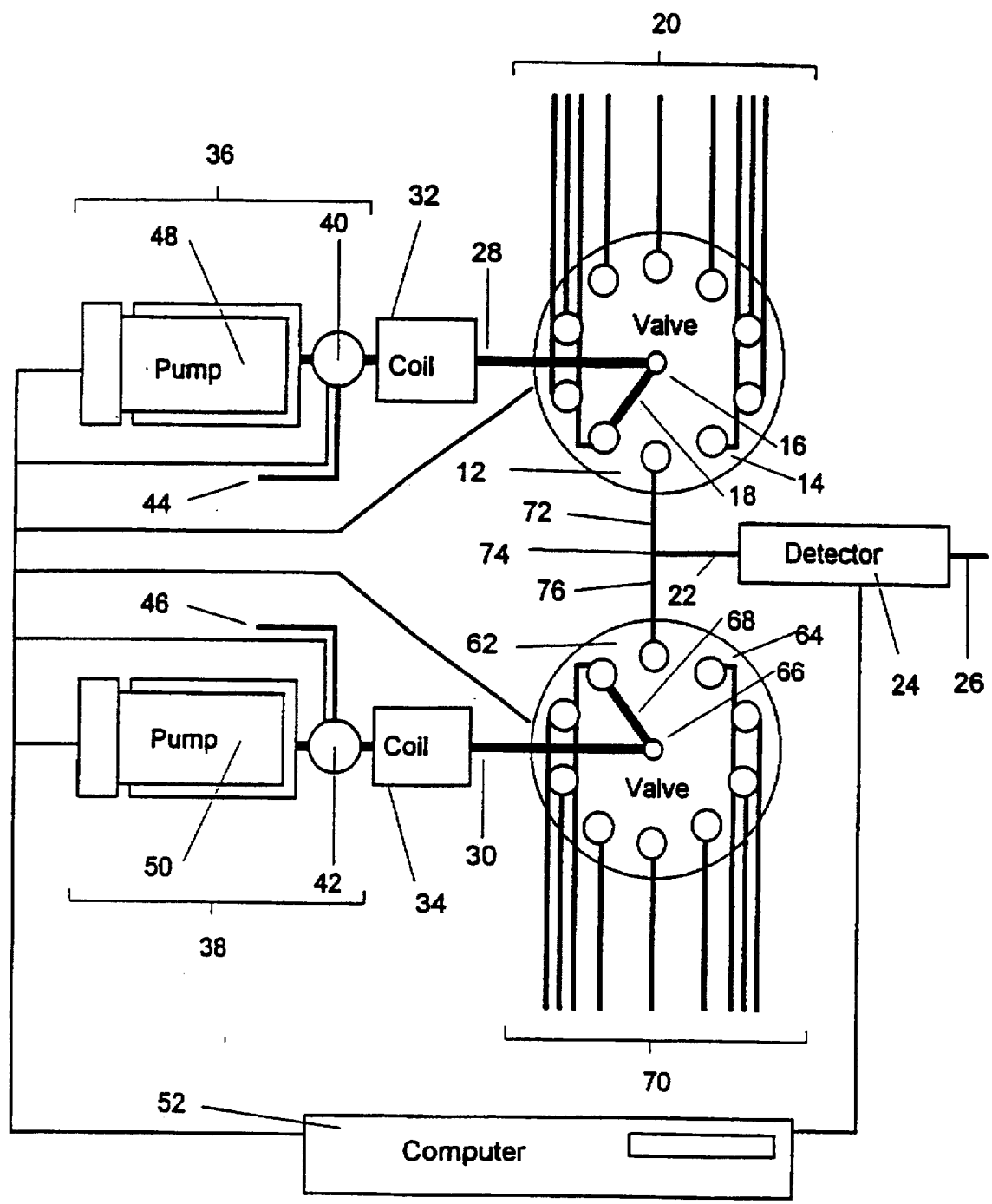
FIG. 3 represents a diagrammatic layout of a flow analysis network apparatus of a further embodiment according to the invention.

FIG. 3 shows a flow analysis network which can also execute the experimental sequences shown in FIGS. 7(A) and 7(B), but at twice the speed due the two independent pump and valve systems. In this, a first valve hub 12 is comprised of independent ports 14, central access port 16, selector 18, and tubings 20 connected to vessels containing fluids, as for FIG. 1, to detectors, to a waste container or stream, or to other sample processing apparatus. The first central access port 16 is connected via a tubing 28 to a coil 32, and then to a first pumping system 36. The first pumping system 36 is comprised of an access to wash or carrier solution 40, a tubing leading to a wash or earlier solution 44 and the pump itself 48. A second valve hub 62 is comprised of independent ports 64, central access port 66, selector 68, and tubings 70 connected to vessels containing fluids, to detectors, or to other sample processing apparatus. The second central access port 66 is connected via a tubing 30 to a coil 34, and thence to a second pumping system 38. The second pumping system 38 is comprised of a valve access to wash or carrier solution 42, a tubing leading to a wash or carrier solution 46 and pump 50. In the embodiment shown, one of ports 14 is connected to a conduit 72 and thence to a merging tee 74. One of the other ports 64 is connected to a conduit 76 and then to merging tee 74. Merging tee 74 is also connected via another conduit 22 to a detector 24. Where the detector 24 is a flow-through detector, the effluent from the detector then goes to waste 26. In some process applications, the waste stream 26 may be returned to the process. All active components are controlled via a control computer 52. The attributes of coils 32 and 34 are the same as discussed for FIG. 1. Other interconnections of other pairs of ports similar to 14 and 64 may be readily made and the inclusion of sample processing apparatus or detection apparatus within these interconnections.

As an example of how speed improvements are obtained over the network shown in FIG. 3, samples/standards and reagents sequences can be simultaneously entrained within the two holding coils, before merging the two prepared streams at a common tee-piece en route to the detector. This configuration is also better suited to the presence of chemical substances that would be inappropriate to keep in close proximity. An additional advantage would accrue in the handling of radioactive substances, where one valve hub could be kept free of radionuclides, thus providing improved ease of servicing.

An example of the operation of the apparatus shown in FIG. 3

The system may facilitate the overlap pattern shown in FIG. 7(B) in the following manner. Both halves of the system are primed according to the scheme set out for FIG. 1.

Zones of sample and standard are entrained in coil 32 by pump 36 through valve hub 12 in the same manner as for FIG. 1. Simultaneously, zones of reagent one, reagent two and reagent one again are entrained in coil 34 by means of second pump 38 and second valve hub 62. Then valve hub 12 selects port 14 connected to conduit 72 and then to tee-piece 74, detector conduit 22, and detector 24. Simultaneously, second valve hub 62 selects port 64 which is also connected through to tee-piece 74, via conduit 76, and then to detector conduit 22 and detector 24. Then, pump one 36 pushes the sample and standard plugs from coil 32 through conduit 28, valve hub 12, and to tee-piece 74. Simultaneously, second pump 38 pushes the entrained reagent zones from coil 34, through conduit 30, valve hub 62 and to tee-piece 74. The zones from each pumping system overlap at the tee-piece in the manner shown in FIG. 7(B). Reaction occurs, and the resulting train of overlapped zones is passed through to the detector. This results in regions of information from initial baseline, sample background, product from reaction of reagent #2 with sample #1, product from reaction of reagent #1 with sample #1, product from reaction of reagent #1 with standard #1, product from reaction of reagent #2 with standard #1, standard background and post reaction baseline. There are five interaction regions where further mixed solutions are found. These are the sample #1 dilution region, reagent #2 dilution region, reagent #1/reagent #2 overlap region, sample #1/standard #1 overlap (spike) region, and standard #1 dilution region. Any or all of these regions may be used to obtain useful analytical information via the detector.

Figure 4:
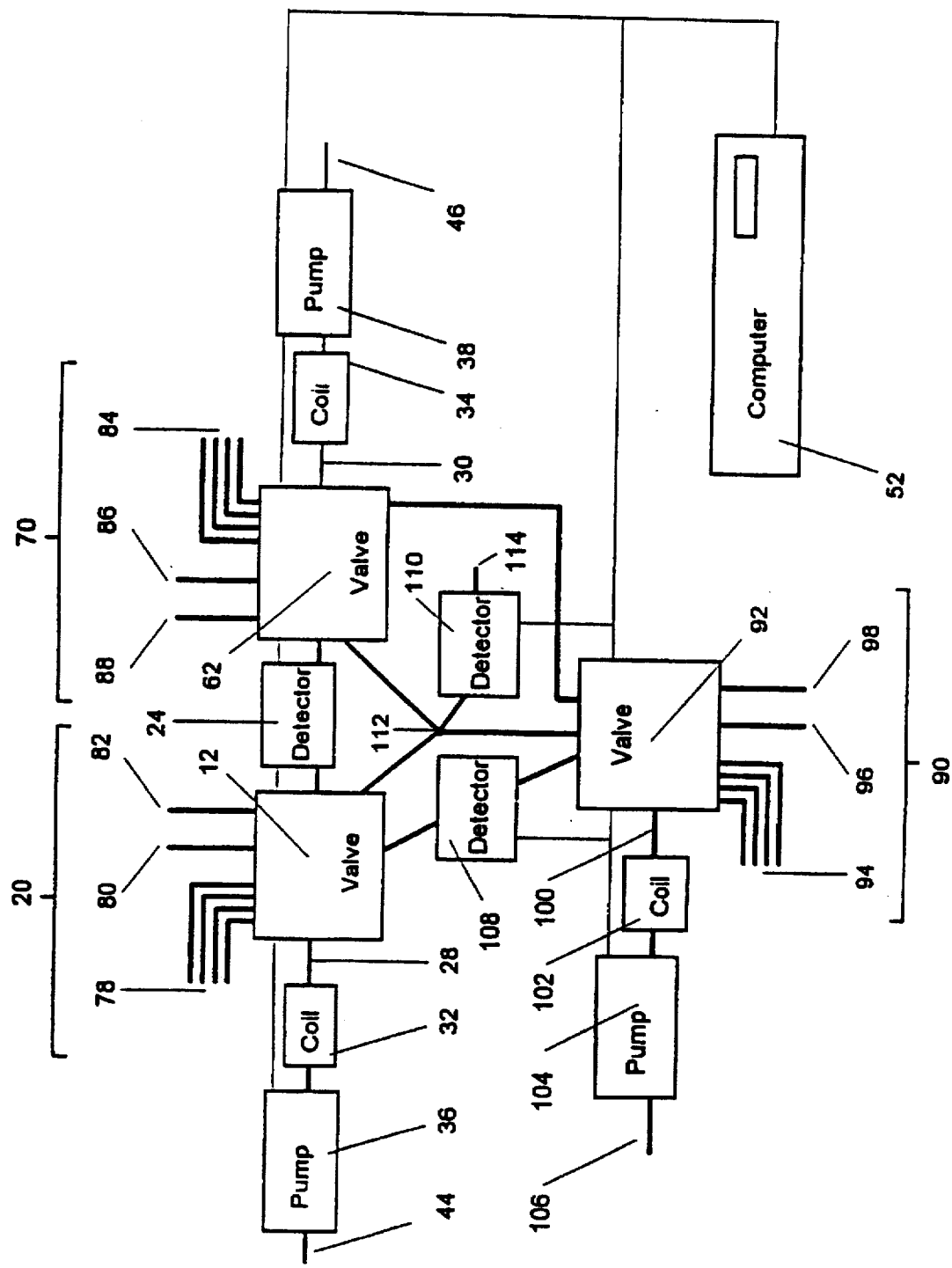
FIG. 4 represents a diagrammatic layout of a flow analysis network apparatus of a yet further embodiment according to the invention.

With reference now to FIG. 4, the apparatus shown is comprised of three cooperant bi-directional pumps and three stream selection hubs wherein various fluids and detectors are arranged around the hubs. The hubs share at least one common connection to allow the fluids to pass from one hub to another, or for a combination of fluids from two or more hubs to mix, or for mixed or unmixed fluids to be passed to one or more detectors. The active components of the system are controlled by a computer.

FIG. 4 shows one implementation of a flow analysis network comprised of three valve hubs and three pumping systems. Each pumping system is associated with a single valve hub. The first such combination is comprised of wash/carrier source 44, pump means 36 (which may be of syringe pump design, peristaltic design or other design, and may include valve means to access one or more wash/carrier source(s) 44), stacking/reaction coil 32, conduit 28, and valve assembly 20 comprised of valve hub 12 to which are connected tubes to wash solution 80, waste 82, and various other fluids 78 including any of samples, standards, reagents, buffers and modifiers. The second such combination is comprised of wash/carrier source 46, pump means 38 (which may be of syringe pump design, peristaltic design or other design, and may include valve means to access one or more wash/carrier source(s) 46), stacking/reaction coil 34, conduit 30, and valve assembly 70 comprised of valve hub 62 to which are connected tubes to wash solution 86, waste 88, and various other fluids 84 including any of samples, standards, reagents, buffers and modifiers. The third such combination is comprised of wash/carrier source 106, pump means 104 (which may be of syringe pump design, peristaltic design or other design, and may include valve means to access one or more wash/carrier source(s) 106), stacking/ reaction coil 102, conduit 100, and valve assembly 90 comprised of valve hub 92 to which are connected tubes to wash solution 96, waste 98, and various other fluids 94 including any of samples, standards, reagents, buffers and modifiers. The valve hubs are interconnected to form a flow network. Detectors or sample processing apparatus 24, 108 are shown positioned on the interconnections between hubs 12 and 62, and hubs 12 and 92. In FIG. 4, valve hubs 62 and 92 are shown as having a straight-through connection. One or more straight-through connections may be facilitated between any pairs of valve hubs. Further detection or sample processing means may be included in this straight-through connection, within any of the conduits 28, 30, 102, any of the coils 32, 34, 102, or on any of the lines 78, 84, 94 associated with valve hubs 12, 62 and 92. Additionally, each of valve hubs 12, 62, and 92 are connected to a confluence point 112 at which streams from all three hubs may be overlapped and sent through to detector 110, and then to waste 114. As hereinabove described, all active components, including valve hubs 12, 62, 92; pumping systems 36, 38, 104; detectors or sample processing apparatus 24, 108, 110, are controlled by control computer 52.

A basic example of how this apparatus functions is as given for FIG. 7(C) hereinbelow, where the three pumping systems are each used to prepare a set of stacked zones and then simultaneously merge and mix en route to the detector attached to the central node. This system includes a central confluence point 112 at which solutions from each of the three pump means 36, 38 and 104 stacked in coils 32, 34 and 102 can flow through conduits 28, 30 and 100, and meet and, as necessary, flow to a detector 110 and then to waste 114. This allows for more complex zone overlap protocols than is shown in FIGS. 7(A) and 7(B). For example, the third pump could be used to intelligently and automatically correct for abnormal sample pH. In research studies, it could be used to overlay different strength or different pH buffers as shown in FIG. 7(C). The third pump could also be used to overlay multiple different interferent species so that automated interference studies would be facilitated. It may further be used to provide a variable, programmable dilution to assist in dealing with high concentration samples.

Each of the valve hubs is similarly configured. Using the first valve hub 12 as an example, it may be connected via its ports to wash stream 80, waste container or stream 82 and multiple various fluid streams, detector apparatus or sample processing apparatus 78. It is connected, usually but not exclusively via the central access port to coil 32 and pumping system 36. Where the pumping system is not connected via the central access port, the port shall be open only to the individual ports surrounding it and the coil and pumping system shall be attached to one of these ports. This configuration allows for use of the valve as a flow-through unit where the flow is generated by either of the other pumping systems and the fluid used by the pumping system most directly coupled to the valve hub in question is separated from the flow by the selector valve mechanism, specifically, the mini-valve through which the pump would dispense fluid is kept closed.

Interconnections between valve hubs may include sample processing apparatus or detection apparatus 24, 108 and 110 or may be "straight through".

As indicated above, versions of air segmented continuous flow analysis, sequential injection analysis, and flow injection analysis are all possible on this flow network apparatus, and these all become progressively more flexible with addition of further pumps and valve systems.

Figure 5:
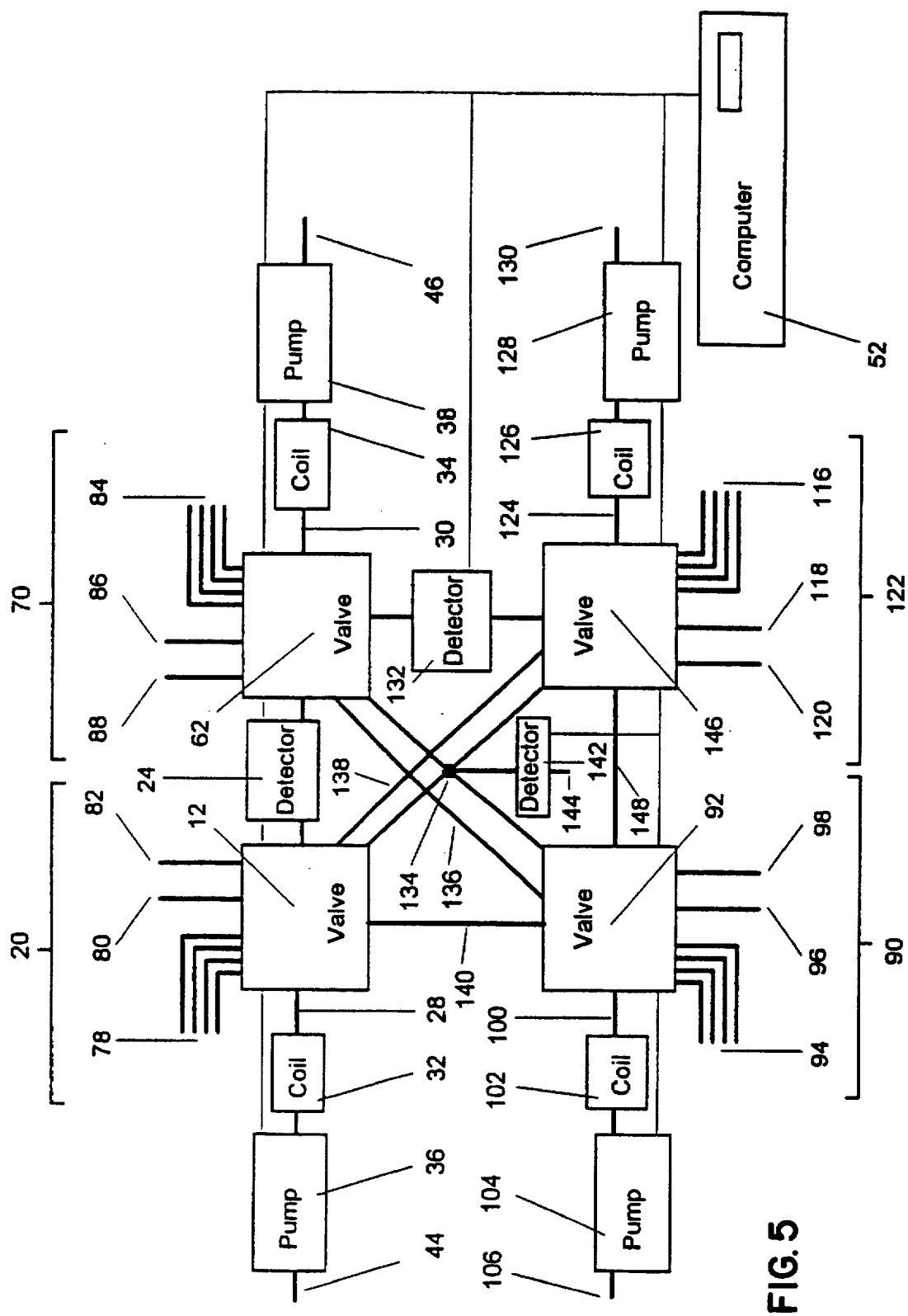
FIG. 5 represents a diagrammatic layout of a flow analysis network apparatus of still yet a further embodiment according to the invention.

With reference to FIG. 5, this shows apparatus which comprises four cooperant bi-directional pumps and four stream selection hubs wherein various fluids and detectors are arranged around the hubs. The hubs share at least one common connection to allow the fluids to pass from one hub to another, or for a combination of fluids from two or more hubs to mix, or for mixed or unmixed fluids to be passed to one or more detectors. The active components of the system are controlled by a computer.

FIG. 5 shows one implementation of a flow analysis network comprised of four valves hubs and four pumping systems. Each pumping system is associated with a single valve hub. The first such combination is comprised of wash/carrier source 44, pump means 36 (which may be of syringe pump design, peristaltic design or other design, and may include valve means to access one or more wash/carrier source(s) 44), stacking/reaction coil 32, conduit 28, and valve assembly 20 comprised of valve hub 12 to which are connected tubes to wash solution 80, waste 82 and various other fluids 78 including any of samples, standards, reagents, buffers and modifiers. The second such combination is comprised of wash/carrier source 46, pump means 38 (which may be of syringe pump design, peristaltic design or other design, and may include valve means to access one or more wash/carrier source(s) 46), stacking/reaction coil 34, conduit 30, and valve assembly 70 comprised of valve hub 62 to which are connected tubes to wash solution 86, waste 88 and various other fluids 84 including any of samples, standards, reagents, buffers and modifiers. The third such combination is comprised of wash/carrier source 106, pump means 104 (which may be of syringe pump design, peristaltic design or other design and may include valve means to access one or more wash/carrier source(s) 106), stacking/reaction coil 102, conduit 100, and valve assembly 90 comprised of valve hub 92 to which are connected tubes to wash solution 96, waste 98, and various other fluids 94 including any of samples, standards, reagents, buffers and modifiers. The fourth such combination is comprised of wash/carrier source 130, pump means 128 (which may be of syringe pump design, peristaltic design or other design, and may include valve means to access one or more wash/carrier source(s) 130), stacking/reaction coil 126, conduit 124, and valve assembly 122 comprised of valve hub 146 to which are connected tubes to wash solution 118, waste 120, and various other fluids 116 including any of samples, standards, reagents, buffers and modifiers. The valve hubs are interconnected to form a flow network. Detectors or sample processing apparatus 24, 132 are shown positioned on the interconnections between hubs 12 and 62, and hubs 62 and 146.

In FIG. 5, valve hub pairs 12 and 92, 12 and 146, 62 and 92, and 146 and 92, are all shown as having a straight-through connections 140, 138, 136 and 148, respectively. One or more straight-through connections may be facilitated between any pairs of valve hubs. Further detection or sample processing means may be included in any straight-through connection, within any of conduits 28, 30, 102, 124, any of coils 32, 34, 102, 126, or on any of lines 78, 84, 94, 116 associated with valve hubs 12, 62, 92 and 146. Additionally, each of valve hubs 12, 62, 92 and 146 are shown connected to a 4-way confluence point 134 at which streams from all three hubs may be overlapped and sent through to detector 142, and then to waste 144. The design shown does not preclude use of lesser designs involving confluences of fewer than four streams or valve hubs which are not connected to a common confluence point. As hereinabove described all active components, including valve hubs 12, 62, 92; 146, pumping systems 36, 38, 104; 128, detectors or sample processing apparatus 24, 132, 142, are controlled by control computer 52.

A basic example of how this apparatus functions is as given for FIG. 7(D) below, where the four pumping systems are each used to prepare a set of stacked zones, and then simultaneously merge and mix them en route to the detector attached to the central node. The first set of stacked zones is prepared by valve assembly 20 in conjunction with pump means 36, and according to the same scheme as discussed above for FIGS. 1–4. The second set of stacked zones is prepared by valve assembly 70 in conjunction with pump means 38, and according to the same scheme as discussed hereinabove for FIGS. 1–4. The third set of stacked zones is prepared by valve assembly 90 in conjunction with pump means 104, and according to the same scheme as discussed hereinabove for FIGS. 1–4. The fourth set of stacked zones is prepared by valve assembly 122 in conjunction with pump means 128, and according to the same scheme as discussed hereinabove for FIGS. 1–4. Indeed, all of the discussions in principal pertaining to the system in FIG. 4 applies to this FIG. 5 embodiment. The connections shown are inferred by the tetrahedron shown in FIG. 8. The confluence point 134 may be selectable from any two, or more valves, and two or more pumps can be used to merge flows and send them to detector 142 and wash 144.

FIG. 6 details designs for valve hubs, based on star geometry and linear geometry. Similarly as seen with electronic networks, other geometries are possible and will have advantages for different applications.

FIG. 6(a) shows the star-geometry valve design 202 used in conventional sequential injection analysis and sold by Valco (Gig Harbor, Wash.) and Rheodyne (Cotati, Calif.). This comprises a central access port 206 connected sequentially to each of a set of ports 204 located around the central port by rotation of a channel 208 in one or in both directions. Fluid can then flow through conduit 210 and a single selected port 204 via central port 206.

FIG. 6(b) shows a star-geometry valve design 212 which has no rotating element. A confluence point 216 is connected to all ports 214. Each port is equipped with its own mini-valve to allow the port to open and close. Flow may occur between any selected port 214 and external conduit 220 through the portion of the star of flow channels 218 internal to the valve hub which lies between any selected port 214 and external conduit 220.

FIG. 6(c) shows a star-geometry valve design 222 similar to that in FIG. 6(b), but where more than one port may be open at one time. Thus, for example, for systems with two pumps where one pump is able to pull a first fluid through a selected port 224 at a flow rate of 2 ml/min and a second pump may push fluid at a flow rate of 1 ml/min through conduit 228 attached to central port 226, then a second fluid is drawn by flow rate difference at a rate of 1 ml/min through a second open port 224. This facilitates mixing of said first and second fluids at confluence point 226 and within external conduit 230.

FIG. 6(d) shows a star-geometry valve design 232 without a central port, where all access is via peripheral ports 234, wherein each has its own OPEN-CLOSE mini-valve. Fluids flow through internal conduits 238 only when at least two ports are simultaneously open. External connections 240 may be to any port 234.

FIG. 6(e) shows a linear-geometry valve design with multiple mini-valves arranged linearly along a central conduit 246. Solutions enter and leave the conduit via one or more exit ports 244 and exit ports 254 connected to individual mini-valves 252, 256. Each mini-valve is of an OPEN-CLOSE design having two ports 248, 250. All valves are mounted on a common manifold block 258. More than one valve 252, 256 may be OPEN at one time, thus allowing mixing by two or more flowing streams and random injection operations. The exit port 244 may be blocked where access is to be only via the mini-valves, in which case at least two mini-valves must be OPEN for flow to occur. The valve bodies 242 are mounted into block 258 as shown in the side-on drawing.

FIG. 6(f) shows a linear-geometry valve design, similar to that of FIG. 6(e), but with multiple mini-valves arranged in offset fashion so as to decrease the length of the internal conduit required to mount the required number of mini-valves. Exit port 260 is connected to common central conduit 262, with which individual valves 268, 272 and 274 are in contact. Each mini-valve is of an OPEN-CLOSE design to allow flow between its two ports 264, 266 when the valve is in the OPEN position. The mini-valves are mounted on a common manifold block 276. The exit port 260 may be blocked where access is to be only via the mini-valves, in which case at least two mini-valves must be OPEN for flow to occur. The valve bodies 278 are mounted into block 276 as shown in the side-on drawing.

FIG. 6(g) shows a linear-geometry valve design with multiple mini-valves arranged in a fashion that allows multiple valves 280 to access the same position along central conduit 284. The manifold block 282 is shown as square, but may be hexagonal, or of other design so long as the entry and exit ports can all be machined. If octagonal, the valve hub would be equivalent to a massively parallel version of the design shown in FIG. 6(c). The exit port 286 may be blocked where access is to be only via the mini-valves, in which case at least two mini-valves must be OPEN for flow to occur.

FIG. 7(A) shows an overlap protocol between a set of segments 300 stacked by a first pump and a set of segments 302 stacked by a second pump, as may be achieved by any of the apparati illustrated in FIGS. 1–5. The first set of stacked segments 300 has the sequence Wash.-Sample #1-Standard #1-Wash. The second set 302 has the sequence Wash.-Reagent #1-Wash. This overlap results in regions of information from initial baseline 304, sample background 306, product from reaction of reagent #1 with sample #1 308, product from reaction of reagent #1 with standard #1 310, standard background 312, and post reaction baseline 314. There are five interaction regions where further mixed solutions are found. These are the sample #1 dilution region 316, reagent #1 dilution region 318, sample #1 standard #1 overlap (spike) region 320, reagent #1 dilution region 322, and standard #1 dilution region 324. Any or all of these regions may be used to obtain useful analytical information via the detector. The issue of internal standardization accompanying every result is important since it goes further towards guaranteeing analytical quality i.e. the certainty that the answer given is the correct answer and analysis integrity i.e. the certainty that the analysis is being performed under accepted conditions or within accepted limits.

FIG. 7(B) illustrates a slightly more complicated system, where two reagents are included. Again, two sets of entrained zones are overlapped at a confluence point, as may be achieved by any of the apparati shown in FIGS. 1–5. The first set of zones 330 contains the sequence Wash.-Sample #1-Standard #1-Wash. The second set of zones 332 contains the sequence Wash.-Reagent #2-Reagent #1-Regent #2-Wash. This overlap results in regions of information from initial baseline 334, sample background 335, product from reaction of reagent #2 with sample #1 336, product from reaction of reagent #1 with sample #1 338, product from reaction of reagent #1 with standard #1 340, product from reaction of reagent #2 with standard #1 342, standard background 343, and post reaction baseline 344. There are seven interaction regions where further mixed solutions are found. These are the sample #1 dilution region 346, sample #1 reagent #2 dilution region 348, reagent #1/reagent #2/sample #1 overlap region 350, sample #1/standard #1 overlap (spike) region 352, reagent #1/reagent #2/standard #1 overlap region 354, standard #1/reagent #2 dilution region 356, and standard #1 dilution region 358. Any or all of these regions may be used to obtain useful analytical information via the detector. The issue of internal standardization accompanying every result is again addressed within each analysis. This situation, as drawn, would allow determination of two analytes present in the sample and two-component standard solution. Alternatively, it could be used for a chemistry that required two reagents, such as the classical molybdenum blue method for determination of phosphate.

FIG. 7(C) shows an overlap of three sets of stacked zones, as could be achieved by the apparatus shown in FIGS. 4 and 5. In this, a stream containing an entrained segment of sample is merged with a second stream containing an entrained segment of reagent, and with a third stream containing a concentration gradient of a pH modifier. In an alternative embodiment, the concentration gradient of pH modifier would be replaced by a concentration gradient of interferent. While the gradients shown are linear, nothing shall prevent non-linear gradients from being used. The first set 360 contains Wash-Extended Sample #1-Wash. The second set 362 contains Wash-Extended Reagent #1-Wash. The third set 364 contains Wash-Decreasing Slope of pH Modifier 368-No pH Modifier 370-Increasing Slope of pH Modifier 372-Wash. 374. There are two dilution regions, early 367 and late 373 in the sequence, which would be difficult to interpret, since Sample #1, Reagent #1 and pH Modifier are all simultaneously decreasing in concentration. Regions 368 and 372 allow the user to determine the effect of pH on the reaction of Sample #1 with Reagent #1. In research studies, this allows the stability of products formed to be determined. In routine analytical procedures, this will allow the effect of abnormal sample pH to be detected and potentially compensated for.

Experimentally, regions 368 and 372 are not equivalent wherever the reaction time allowed for region 368 is different to that of region 372. Longer reaction times allow reactions to proceed further towards completion. Where sequential reactions occur, longer reaction times allow probing of the later reaction. Thus, limited kinetic information is provided in several ways.

Where reaction between Sample #1 and Reagent #1 is reversible and pH dependent, then the overlap shown here could be produced by the apparati shown in FIGS. 1–3. To achieve this, Sample #1 and Reagent #1 are fully overlapped and stored within the first coil/pumping system. The second coil/pumping system is used to set up the pH modifier gradient. The two stacks are then merged to achieve the same effect as shown in FIG. 7(C). As noted above, an interferent or other chemical modifier may be substituted for the pH modifier to achieve different chemical information from the same experimental sequence.

Figure 7D:
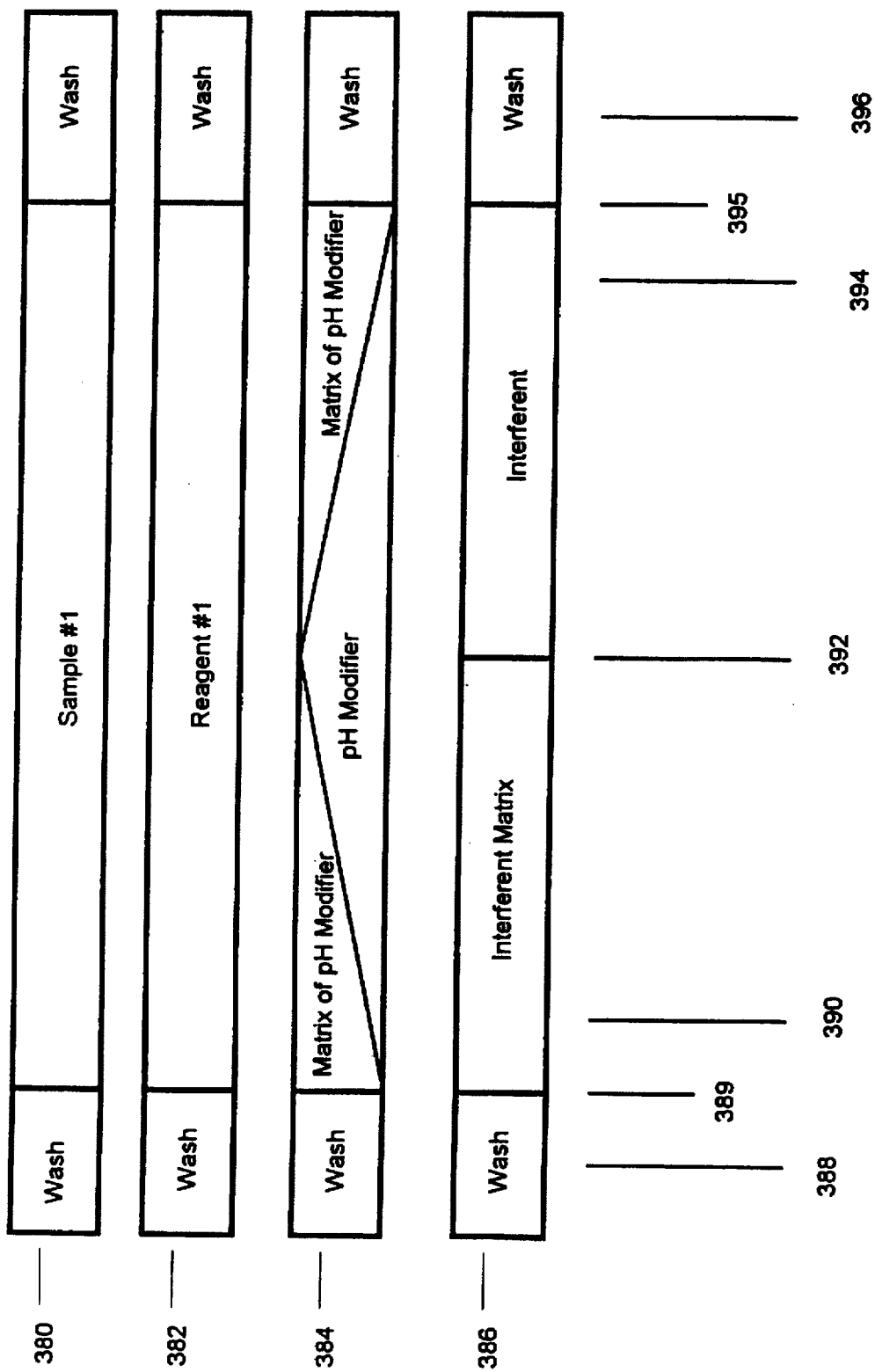
FIG. 7(D) represents an alternative embodiment of an advanced operation mode for a flow network apparatus of the invention with at least four pumping systems.

FIG. 7(D) shows the overlap of four stacks, as may be achieved by the apparatus shown in FIG. 5. In this, a stream containing an entrained segment of sample, is merged with a second stream containing an entrained segment of reagent, and with a third stream containing a concentration gradient of a pH modifier, and with a fourth stream containing entrained segments of interferent matrix and interferent. In an alternative embodiment, the pH modifier and interferent could be exchanged. While the gradients shown are linear, nothing shall prevent non-linear gradients from being used. The first stack 380 contains Wash-Extended Sample #1-Wash. The second stack 382 contains Wash-Extended Reagent #1-Wash. The third stack (384) contains Wash-Increasing Gradient of pH Modifier-Decreasing Gradient of pH Modifier-Wash. The fourth stack 386 contains Wash- Interferent Matrix-Interferent-Wash. The interferent matrix solution is the same solution in which the interferent is present but minus the interferent-typically it is a buffer solution. The regions of information available are therefore Wash 388, Effect of pH on reaction of Reagent #1 with Sample #1 390, Effect of Interferent on reaction of Reagent #1 with Sample #1 at different pH's 394, and Wash 396. Other overlap zones present are an early general dilution region 389, interferent dilution region 392 and late general dilution region 395.

Many different overlap patterns with three or four components can be generated by systems with three or four pumps. More complex overlaps can be generated by multi-step overlapping, i.e., by generating and storing sets of overlapped zones, and then overlapping these.

Figure 8:
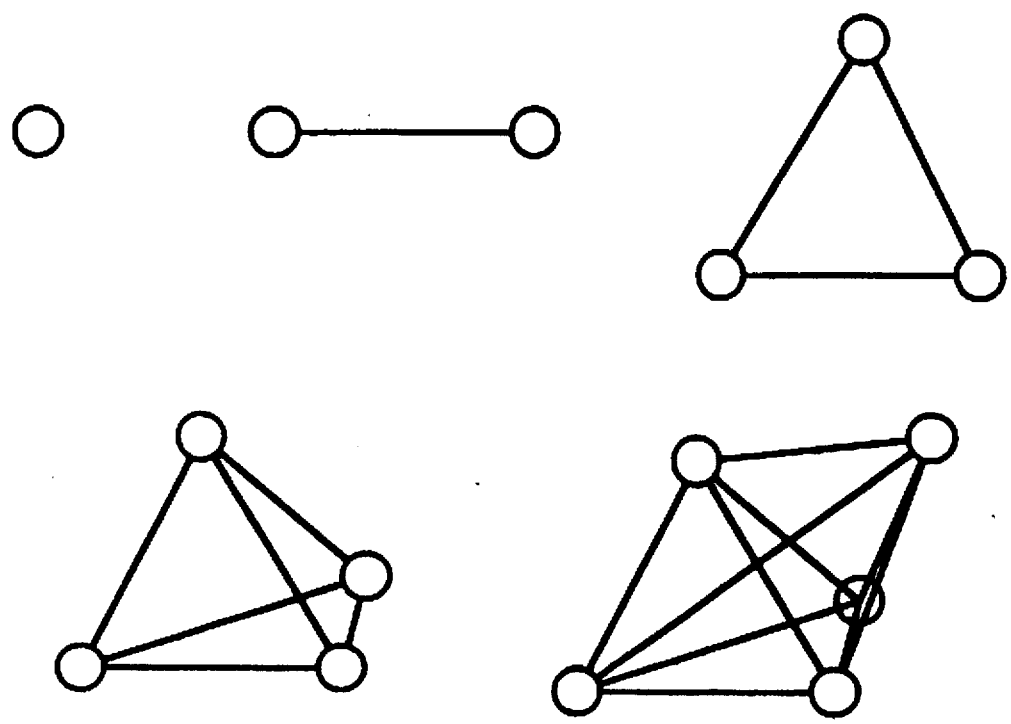
FIG. 8 schematically illustrates possible connections for flow networks of two to five valve hubs, increasing in complexity.

FIG. 8 shows the evolution of increasingly complex networks. For completeness, a one valve hub system is also shown, but it is not a network since it is singular. The two valve hub design is only a network if flow is intended to be allowed in both directions between the valve hubs, and chemical information is maintained by adequate separation of segments during these transfers. In each case, the n dots (vertices) form a regular shape in n–1 dimensional space. Extensions to higher numbers of vertices are possible. Each dot (vertex) can be considered physically as a multiport valve, actually having more ports than the number of lines entering and leaving it. Alternatively, each dot may be considered as one pumping system, with interconnecting lines indicating potential interconnections between pumping systems. The most versatile networks are symmetric wherein each side is of the same length, complete wherein all vertices are connected to all others and fully bi-directional i.e. flow can occur in either direction between valves. Less versatile networks would be asymmetric, incomplete, and/or involve unidirectional links. For example, incomplete networks of four vertices would include the square design shown in FIG. 5, in which there were no cross-connections between valve hubs 1 & 3, and 2 & 4, and a linear design where valves were only connected in numerical 1-2-3-4 sequence.

The single vertex figure is not a network. If appropriately configured, the single vertex figure may be considered as one hub—i.e., a representation of conventional sequential injection analysis.

To date, there are no known systems that would be represented by numbers of vertices higher than two.

Figure 9A:
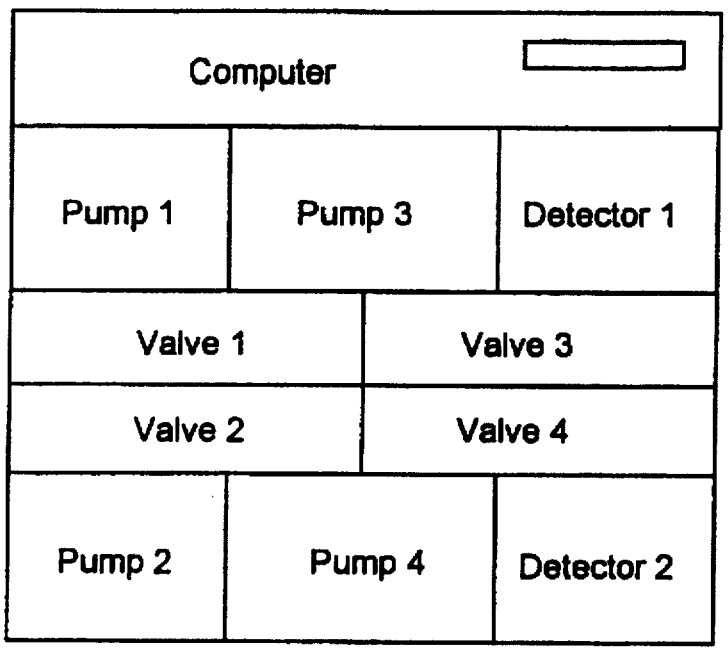
FIG. 9(A) represents a physical design for a four-vertex flow analysis network.
Figure 9B:
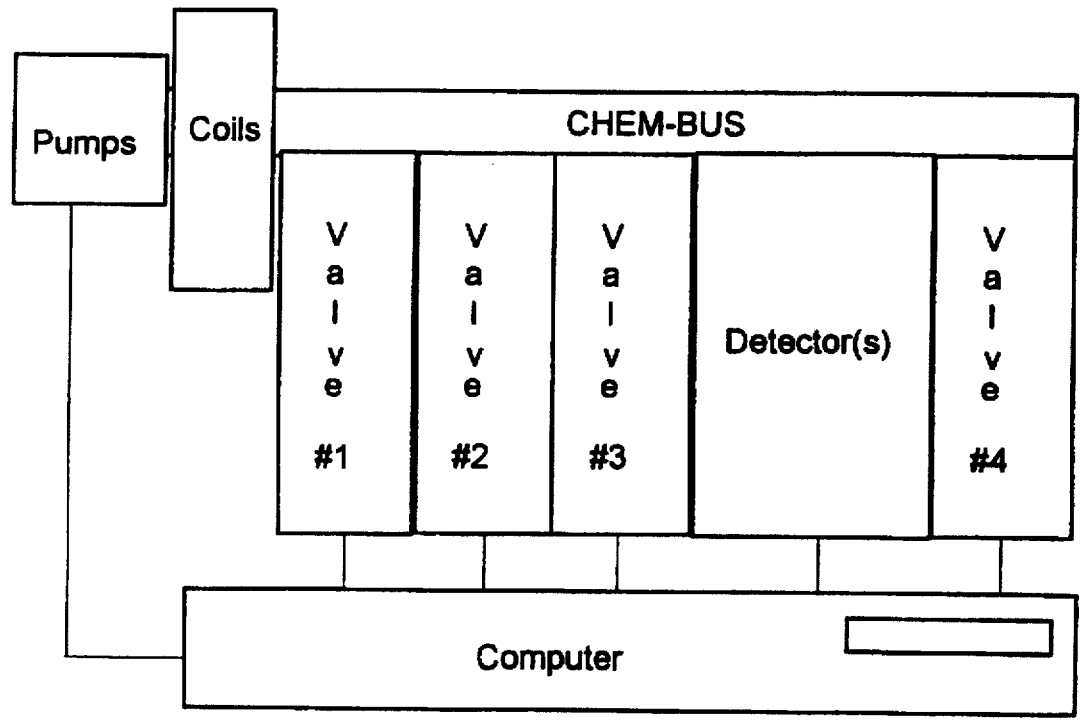
FIG. 9(B) represents an alternative physical design for a four-vertex flow analysis network.

FIGS. 9(A) and 9(B) represents two physical designs for a four-vertex flow network. The optimal physical manifestation of a flow analysis network is one where connection lengths are minimized so as to avoid excessive dispersion. The effects of dispersion can be compensated for by use of larger volumes of sample and/or reagent, but this penalizes the analyzer as far as sample throughput rates and cost and time per analysis are concerned. Larger volumes, however, tend to provide greater signal-to-noise and therefore lower detection limits. This is to be preferred in laboratory use and in field use, where analyte levels may be low. For on-line process use, however, analyte levels can be very high, and thus dispersion and even deliberate dilution can be beneficial to the analysis.

Figure 10:
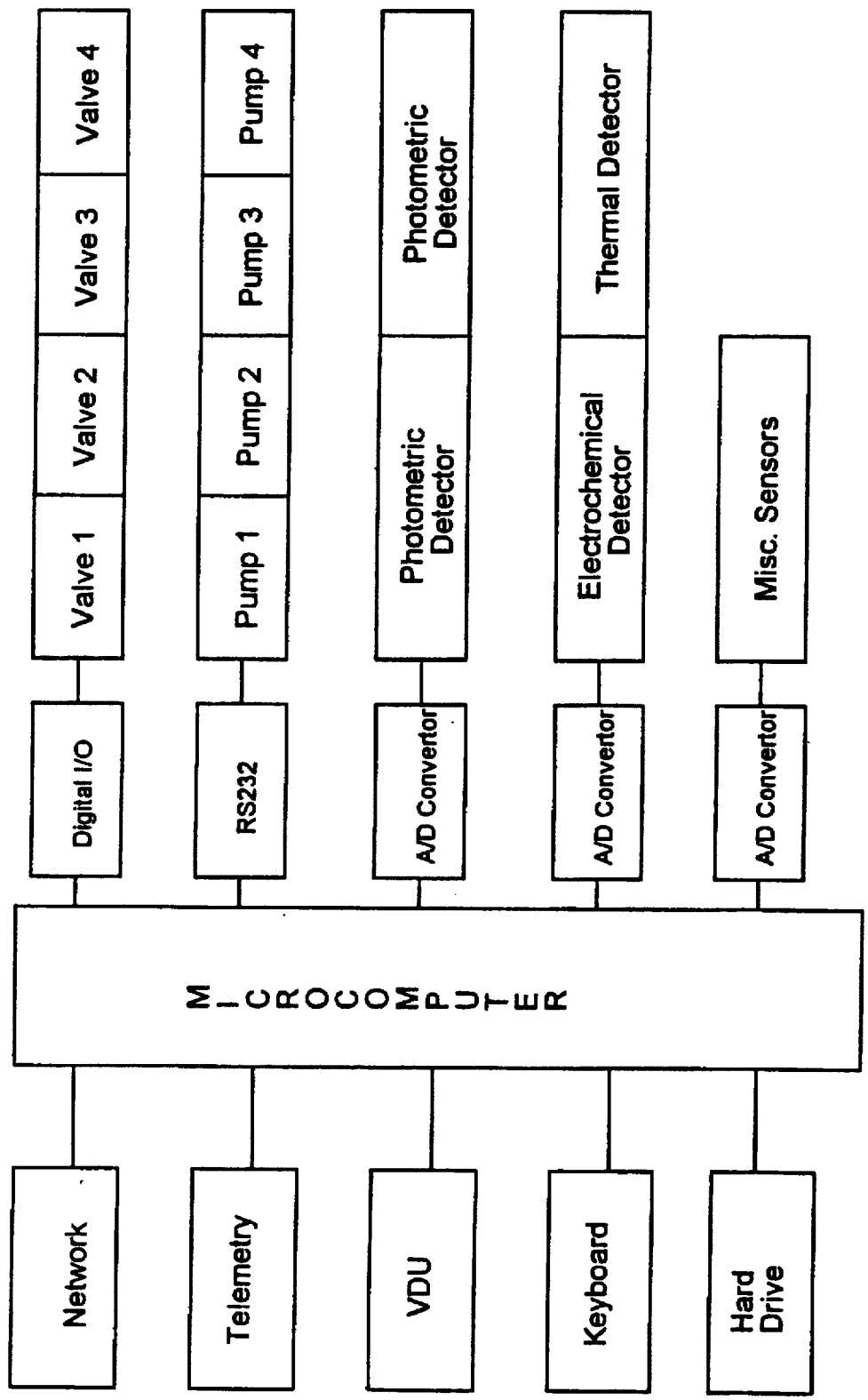
FIG. 10 represents an embodiment of a computer control strategy that can be used to control a four-vertex flow analysis network.
Figure 11:
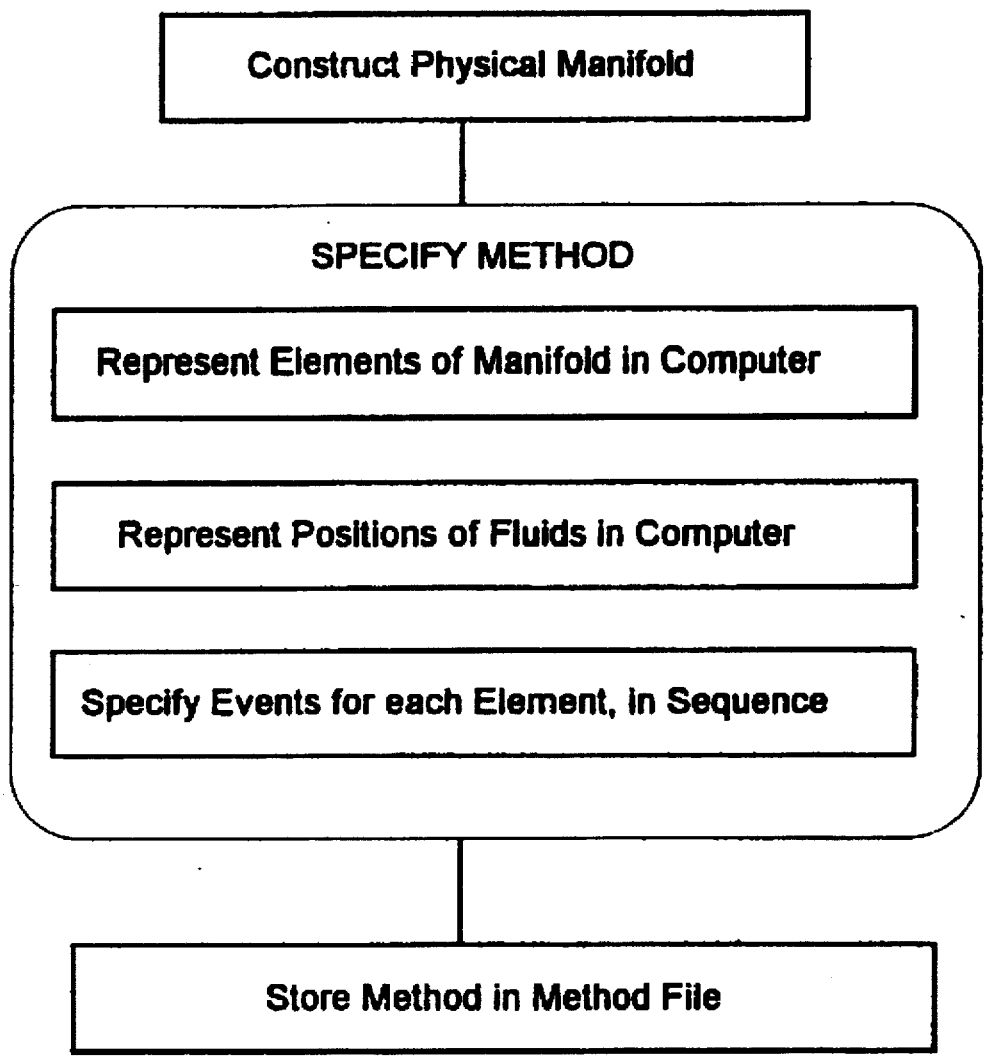
FIG. 11 represents a flow diagram of the operating software for methods specification.
Figure 12:
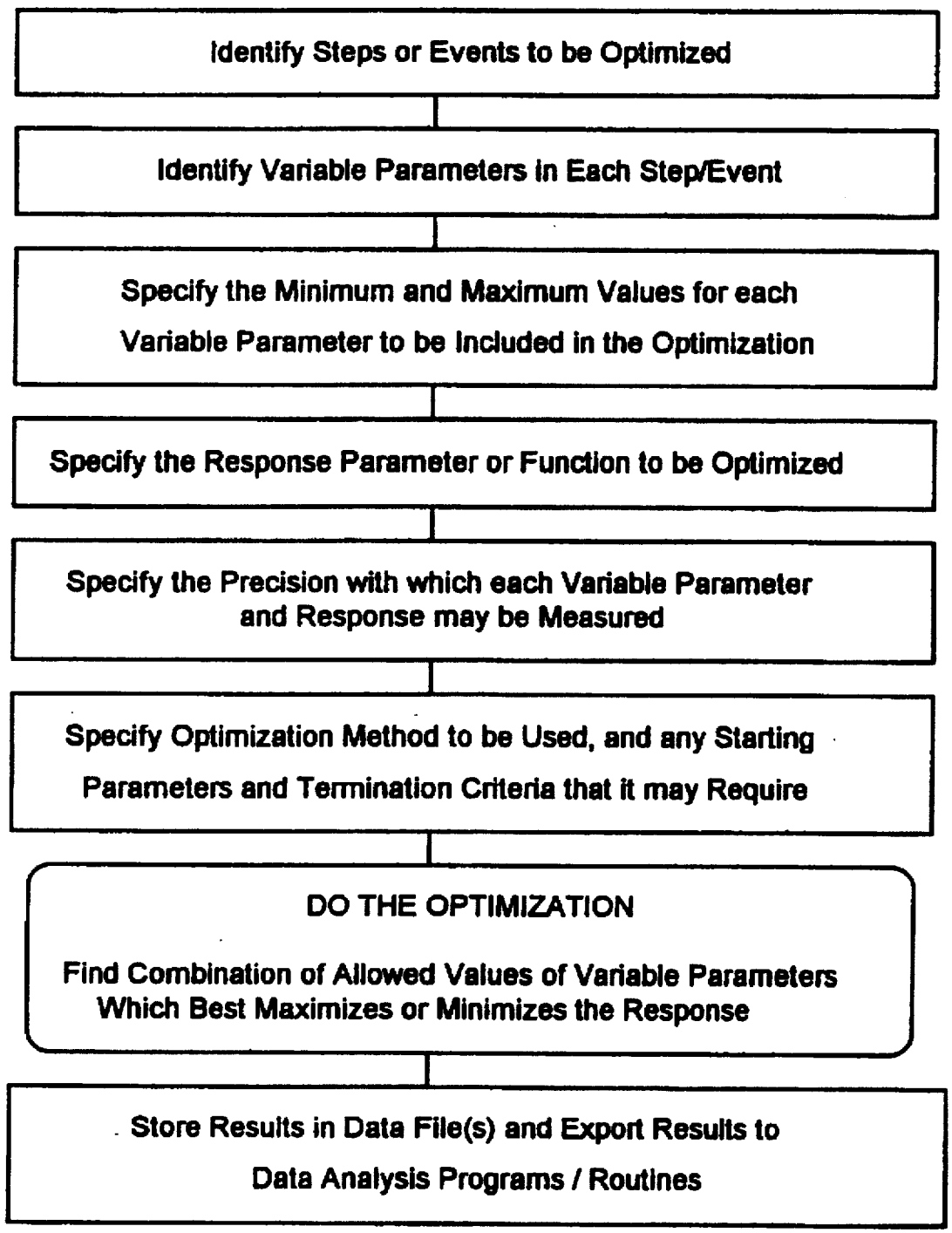
FIG. 12 represents a flow diagram of the operating software for methods optimization.
Figure 13:
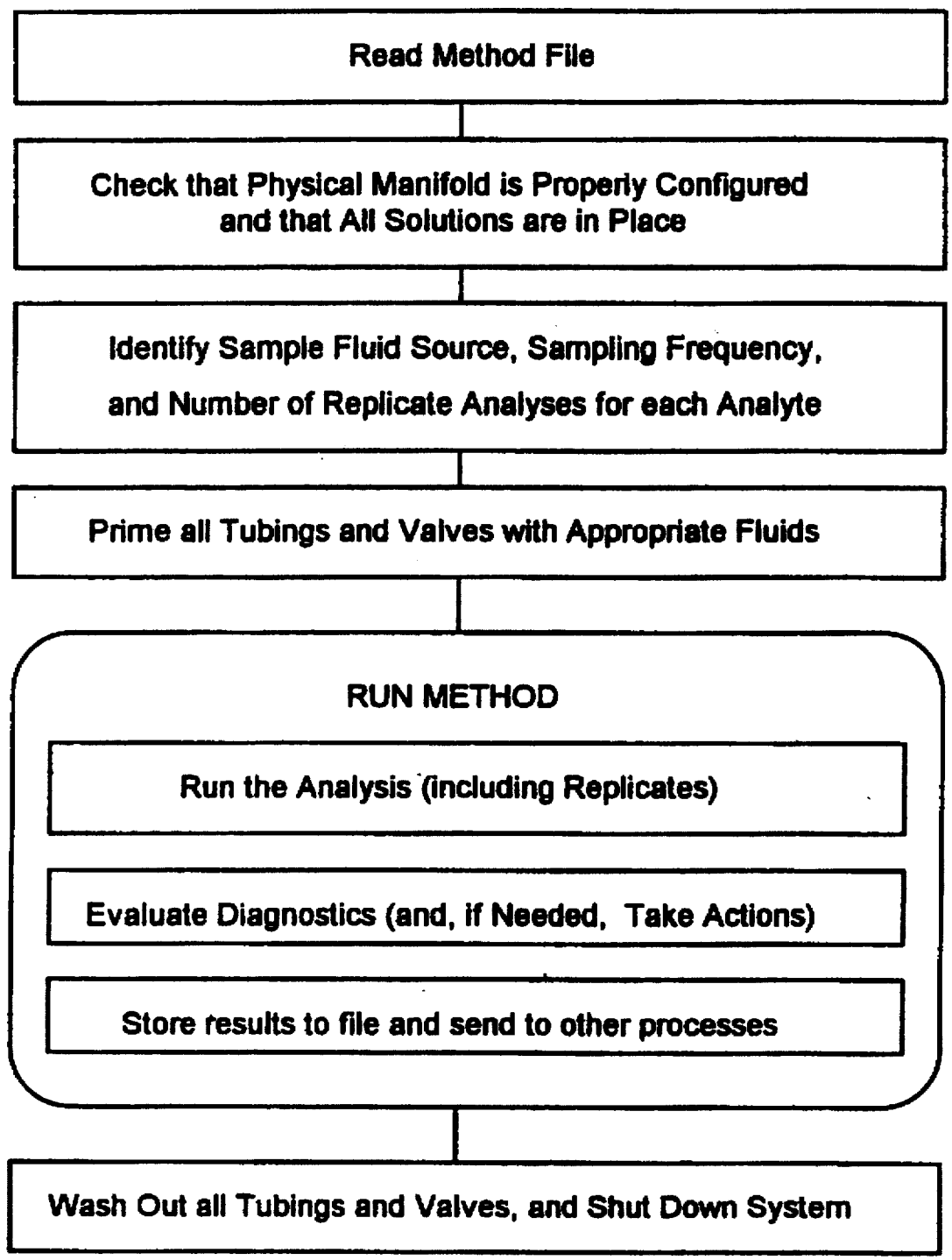
FIG. 13 represents a software flow diagram for running routine analysis.
Figure 14:
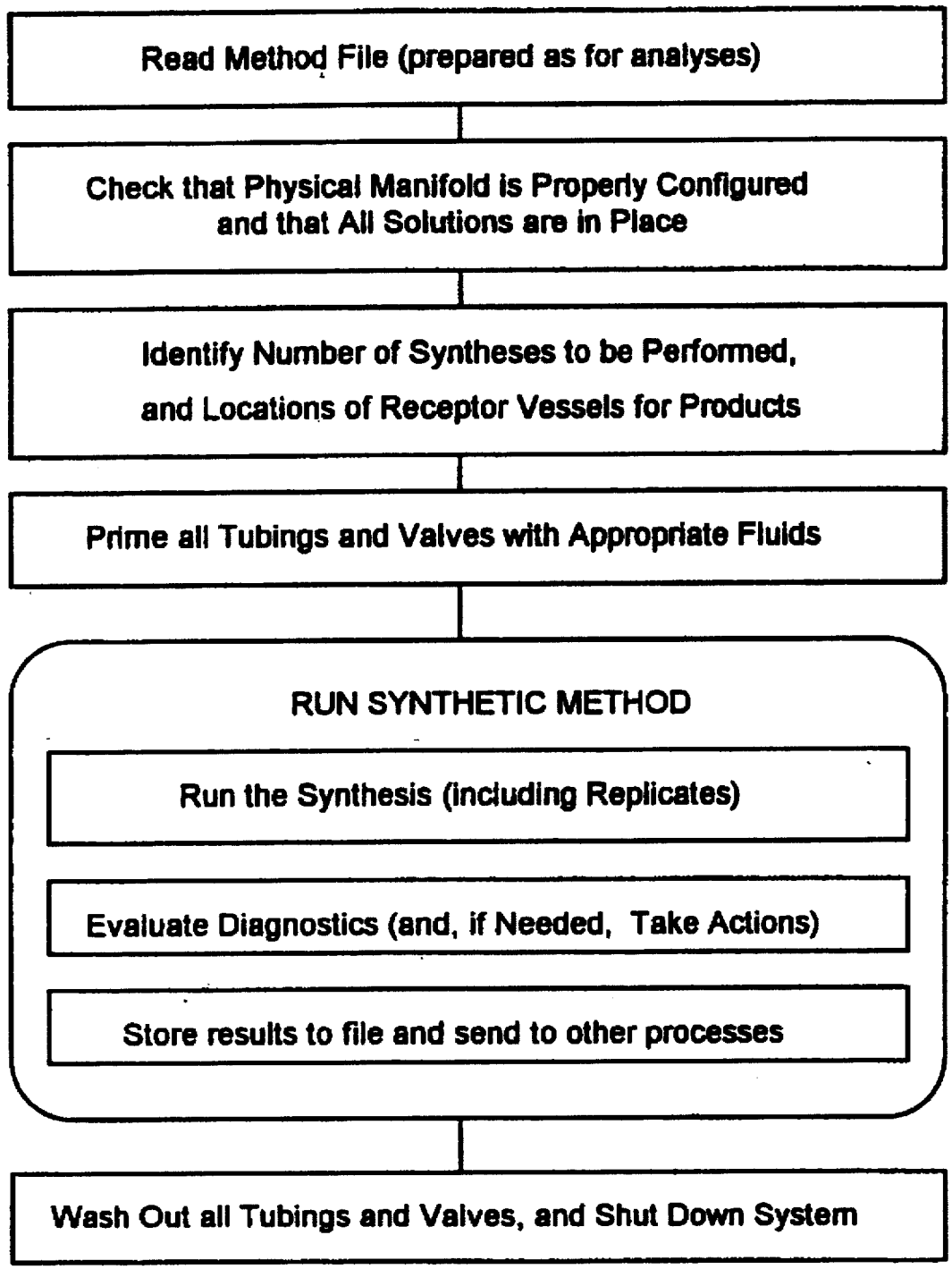
FIG. 14 represents a flow diagram of the operating software for running synthesis methods.

FIG. 10 represents one implementation of the control electronics with embedded software that can be used to control a four vertex flow analysis network.

FIGS. 11–14 represent the algorithms used for software control of the networks.

Figure 15:
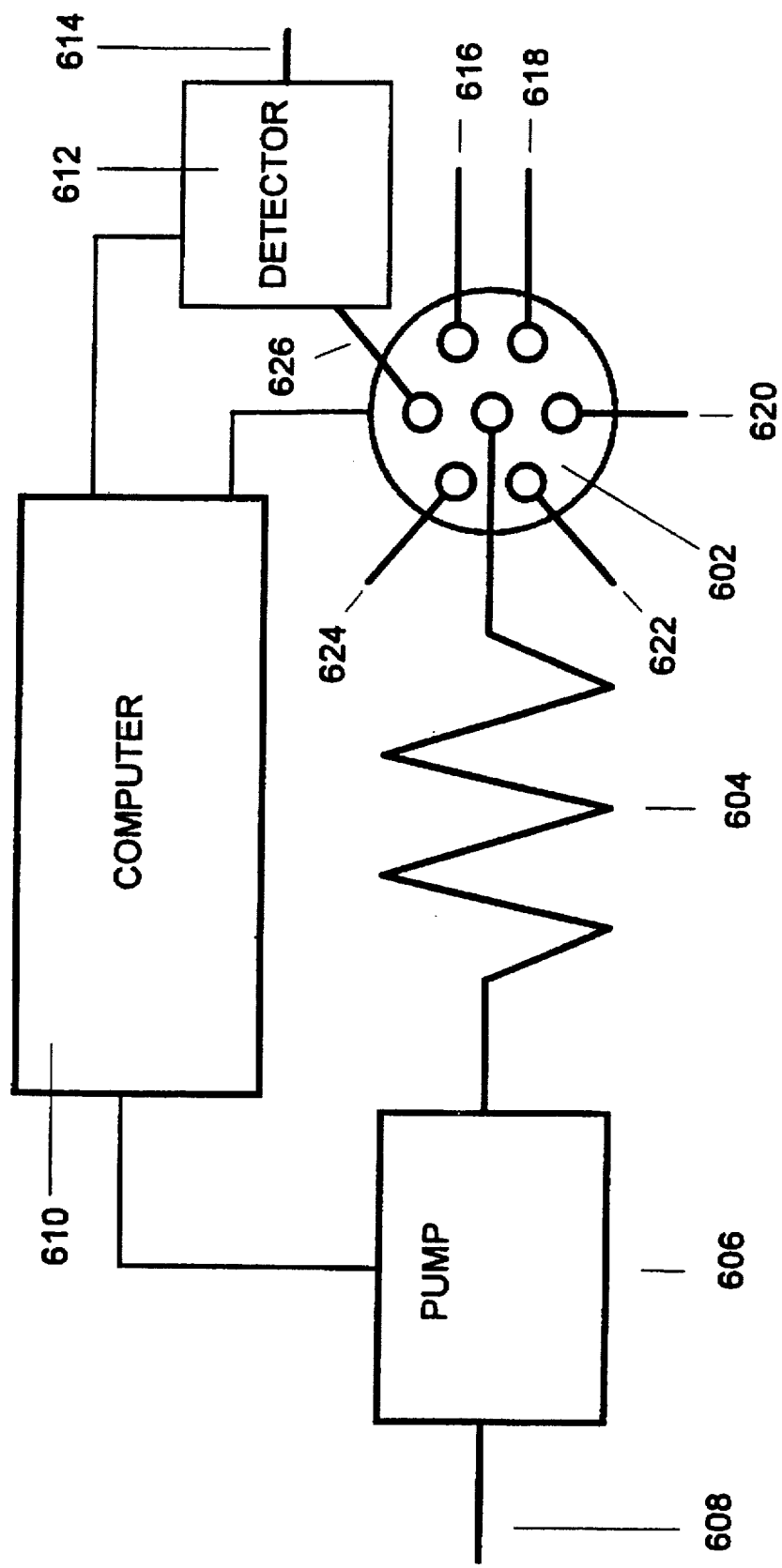
FIG. 15 represents a diagrammatic layout of a sequential injection analyzer according to the prior art; and wherein the same numerals denotes like parts.

FIG. 15 represents an embodiment of a sequential injection apparatus of the prior art.

A sequential rotary valve 602 is connected to a coil 604 and bidirectional pump 606. Pump 606 and valve 602 are controlled by a computer 610. The pump 606 may receive a wash solution via a second connection 608. Joined by a conduit to one of the valve ports 626 is a detector 612, the effluent from which goes to waste 614. Conduits attached to other valve ports 616, 618, 620, 622, 624, may lead to reagent solutions, sample solution, standard solutions, and reactors. The pump 606 and valve 602 work together to stack within coil 604, usually two, abutting zones of reagent and sample or standard solutions taken from tubes attached to any of valve ports 616, 618, 620, 622, 624. Reaction ensues across the reagent-sample interface, and the resulting mixture is then directed to detector 612.

In one embodiment, a sample zone may be sandwiched between zones of two different reagents to provide two reagent-sample interfaces, and hence determination of two analytes present within the sample.

In another embodiment, short zones of two reagents, a buffer and a sample may be introduced in sequence into the coil, where limited, sequence-dependent mixing is possible.

In another embodiment, zones of reactants and sample solution may be selected and sent to a reactor. The contents of the reactor may then be withdrawn and sent to the detector.

The apparatus shown in FIG. 15 is different and inferior to that according to the invention in that the prior art apparatus does not permit the following:

1. It does not facilitate any of the modes of operation given by example in FIGS. 7A–7D.
2. It does not facilitate complete overlap of fluid zones, except within a large volume reactor which results in complete loss of the spatial provided by modes given in FIGS. 7A–7D.
3. It does not facilitate any of the modes of operation that require more than one port to be open simultaneously. The rotary valve is limited such that only one port may be accessed at any one time.
4. It does not facilitate separate simultaneous reaction of multiple samples, for example, in parallel holding coils.
5. It does not facilitate any mode that requires rapid alternation between ports. The rotary design of the valve requires that ports must be accessed in order.
6. It does not facilitate solvent modulation.
7. It does not facilitate continuously variable solvent compositions.
8. Use of a single pump does not facilitate preparation and use of linear concentration gradients by synchronous variations of flow rates. Concentration gradients produced are only by means of mixing chambers or dispersion.
9. It does not facilitate air-segmented continuous flow analysis.
10. It does not facilitate flow injection analysis in that the apparatus has no discrete length of tubing to act as an injection loop.
11. The apparatus shown is not a flow analysis network, since it works in isolation.
12. Its operating software is simple and does not synchronize its operations with the actions of other units.

It is evident from the aforesaid exemplification of apparatus according to the invention that use of larger numbers of networked valves is more versatile than use of a single multiport valve with perhaps 64 ports. Software control of multi-valve systems, however, is inherently more complex. In the systems according to the present invention, each port is preferably independently controlled via a chemically-inert OPEN/CLOSE mini-valve wherein each valve hub uses multiple mini-valves. The mini-valves are controlled, typically, but not exclusively, via 96 digital output lines from a control computer and driver transistors. Each digital output line is optically isolated so as to protect the computer system from any stray voltages and from high currents which might result from shorting within the valves themselves. Each digital output line is also equipped, preferably, with a status light emitting diode (LED) to indicate whether each minivalve is presently open or closed. This provides diagnostic information to technicians and methods developers.

The above discussion does not limit the description of the invention to systems where there are as many valve hubs as there are pumps, nor to systems which have one more pump than valve. Indeed, many combinations are possible, and each will have different attributes and advantages in different use situations.

Although the disclosure describes and illustrates preferred embodiments of the invention, it is to be understood that the invention is not limited to these particular embodiments. Many variations and modifications will now occur to those skilled in the art.

We claim:

1. Flow analysis network apparatus comprising
   at least one multiport valve having a plurality of ports; each of said ports adapted to receive therethrough a selected fluid;
   fluid stacking means wherein a plurality of selected fluids is stacked in predetermined order connected with said valve;
   fluid contacting zones wherein at least two of said selected fluids make contact or combine;
   first mixing means wherein at least two of said selected fluids are capable of being mixed in a single stream of said selected fluids;
   at least one conduit connected with said ports and said fluid stacking means, whereby selected fluids are selectively transferred between said ports and said fluid stacking means;
   pumping means for effecting passage of said selected fluids through said valve, said conduit and said fluid stacking means;
   control means to selectively control passage of selected fluids though said valve;
   port selection means connected with said control means;
   sensing means connected with said control means and said valve;
   the improvement comprising said fluid stacking means comprising at least a first fluid stacking means wherein a first plurality of said zones of selected fluids is stacked in pre-determined order, a second fluid stacking means wherein a second plurality of said zones of selected fluids is stacked in pre-determined order,
   said pumping means comprising at least two independent bi-directional pumps,
   said control means capable of controlling flow of selected fluids through more than one port of said multiport valve simultaneously, wherein said multiport valve is a non-rotary valve,
   computer means to control passage of selected fluids through said multiport valve and
   second mixing means wherein said first and second pluralities of stacked zones are contacted or mixed into a single stream or a selected fluid is contacted or mixed with a plurality of stacked zones into a single stream.

2. Apparatus as defined in claim 1 further comprising a second fluid contact zone wherein selected fluids from at least said first plurality of zones and said second plurality of zones received from said stacking means make contact.

3. Apparatus as defined in claim 1 wherein said pumping means comprises at least a first pump for effecting passage of said selected fluids through said first fluid contact zone and a second pump for effecting passage of said selected fluids through said second fluid contact zone.

4. Apparatus as defined in claim 1 wherein said conduit is connected with each of said ports to allow selected fluids to be selectively transferred between at least two of said ports.

5. Apparatus as defined in claim 2 wherein said second fluid contact zone is connected with at least said first fluid stacking means and said second fluid stacking means to operably effect confluence of fluid streams from at least said first and said second fluid stacking means.

6. Apparatus as defined in claim 1 wherein said fluid stacking means comprises said fluid contact zone.

7. Apparatus as defined in claim 1 wherein said second fluid contact zone operably receives at least said first fluid accessed via a selected said port with at least one fluid connected with at least one of said stacking means.

8. Apparatus as defined in claim 1 wherein at least said first fluid stacking means and said second fluid stacking means are positioned in parallel, each of said stacking means connected with different said ports of said valve and in common with said first pumping means and wherein zones of selected fluids are placed in predetermined order and held for a period of time.

9. Apparatus as defined in claim 1 wherein said multiport valve is adapted to receive, simultaneously, selected fluid flows therethrough from at least two of said ports.

10. Flow analysis network apparatus comprising
    a first multiport valve having a plurality of first ports, wherein said first multiport valve is a non-rotary valve;
    a second multiport valve having a plurality of second ports, wherein said second multiport valve is a non-rotary valve;
    each of said first ports and said second ports adapted to receive therethrough a selected fluid;
    fluid stacking means wherein a first plurality of selected fluids is stacked in predetermined order connected with said first multiport valve;
    first mixing means wherein at least two of said selected fluids are capable of being mixed in a single stream of said selected fluids;
    first conduit connected with said first ports and said second ports, whereby selected fluids are selectively transferred to selected first ports and selected second ports;
    first control means connected with said first valve to selectively control passage of selected fluids therethrough, wherein said first control means is capable of controlling flow of selected fluids through more than one port of said first valve simultaneously;
    second control means connected with said second valve to selectively control passage of selected fluids therethrough, wherein said second control means is capable of controlling flow of selected fluids through more than one port of said second valve simultaneously;
    pumping means for effecting passage of said selected fluids through said conduit, wherein said pumping means comprises at least two independent bi-directional pumps;
    sensing means connected with said first and second control means;

selection means connected with said first and second control means;

computer means to control passage of selected fluids through said multiport valves; and second mixing means wherein said first plurality of stacked fluids is contacted or mixed with a selected fluid or a second plurality of stacked fluids into a single stream.

11. Apparatus as defined in claim 10 further comprising a third multiport valve having a plurality of third ports, each of said third ports being adapted to receive therethrough a selected fluid and third fluid stacking means wherein a third plurality of selected fluids is stacked in predetermined order connected with said third valve;

second conduit connected with said pumping means, said first ports, said second ports and said third ports, whereby selected fluids are selectively transferred to a selected first port, selected second port and selected third port; and third control means connected with said sensing means, said selection means and said third valve to selectively control passage of selected fluids through said third valve.

12. Apparatus as defined in claim 11 wherein said first multiport valve, said second multiport valve and said third multiport valve are in direct contact one with each other through said first conduit and said second conduit.

13. Flow analysis network apparatus comprising a plurality of multiport valves wherein each of said valves has a determined plurality of ports adapted to receive selected fluids therethrough and wherein said multiport valves are non-rotary valves and fluid stacking means wherein a first plurality of selected fluids is stacked in predetermined order connected with said valves;

first mixing means wherein at least two of said selected fluids are capable of being mixed in a single stream of said selected fluids;

conduits connected with at least two of said multiport valves whereby selected fluids are selectively transferred to selected ports of said at least two of said multiport valves;

control means connected with said valves to selectively control passage of selected fluids therethrough, wherein said control means is capable of controlling flow of selected fluids through more than one port of said multiport valves simultaneously;

pumping means for effecting passage of said selected fluids through said conduits, wherein said pumping means comprises at least two independent bi-directional pumps;

sensing means connected with said control means;

selection means connected with said control means;

computer means to control passage of selected fluids through said multiport valves; and second mixing means wherein said first plurality of stacked fluids is contacted or mixed with a selected fluid or a second plurality of stacked fluids into a single stream.

14. Apparatus as defined in claim 1 further comprising one or more processing means connected with said conduit selected from the group consisting of sampling, fluid parameter measuring, fluid mixing, detecting, reacting, diluting, digesting, solvent extracting, distilling, heating, irradiating, sonicating, solventing and diffusing means.

15. Apparatus as defined in claim 10 further comprising one or more processing means connected with said conduit selected from the group consisting of sampling, fluid parameter measuring, fluid mixing, detecting, reacting, diluting, digesting, solvent extracting, distilling, heating, irradiating, sonicating, solventing and diffusing means.

16. Apparatus as defined in claim 13 further comprising one or more processing means connected with said conduits selected from the group consisting of sampling, fluid parameter measuring, fluid mixing, detecting, reacting, diluting, digesting, solvent extracting, distilling, heating, irradiating, sonicating, solventing and diffusing means.

17. Apparatus as defined in claim 10 wherein said second plurality of selected fluids is stacked in predetermined order connected with said second multiport valve.

18. Apparatus as defined in claim 10 wherein at least one of said first multiport valve and said second multiport valve is adapted to receive, simultaneously, selected fluid flows therethrough from at least two of said first ports and at least two of said second ports, respectively.

19. Apparatus as defined in claim 13 wherein at least one of said multiport valves is adapted to receive, simultaneously, selected fluid flows therethrough from at least two of said ports.

20. Apparatus as defined in claim 1, wherein each of said ports is provided with a mini-valve.

21. Apparatus as defined in claim 10, wherein each of said ports is provided with a mini-valve.

22. Apparatus as defined in claim 11, wherein each of said ports is provided with a mini-valve.

23. Apparatus as defined in claim 13, wherein each of said ports is provided with a mini-valve.

* * * * *